(12) United States Patent
Elie et al.

(10) Patent No.: US 12,144,879 B2
(45) Date of Patent: Nov. 19, 2024

(54) COMPOSITIONS AND METHODS FOR ALTERING THE COLOR OF HAIR

(71) Applicant: L'Oreal, Paris (FR)

(72) Inventors: Jennifer Elie, Piscataway, NJ (US); Wonhee Allison Park, Teaneck, NJ (US); Marc Rosenberg, Westfield, NJ (US)

(73) Assignee: L'OREAL, Paris (FR)

( * ) Notice: Subject to any disclaimer, the term of this patent is extended or adjusted under 35 U.S.C. 154(b) by 107 days.

(21) Appl. No.: 17/877,999

(22) Filed: Jul. 31, 2022

(65) Prior Publication Data

US 2024/0041729 A1 Feb. 8, 2024

(51) Int. Cl.
| | | |
|---|---|---|
| *A61Q 5/10* | (2006.01) | |
| *A61K 8/34* | (2006.01) | |
| *A61K 8/365* | (2006.01) | |
| *A61K 8/41* | (2006.01) | |
| *A61K 8/46* | (2006.01) | |
| *A61K 8/92* | (2006.01) | |

(52) U.S. Cl.
CPC .............. *A61K 8/365* (2013.01); *A61K 8/345* (2013.01); *A61K 8/41* (2013.01); *A61K 8/466* (2013.01); *A61K 8/922* (2013.01); *A61K 2800/4322* (2013.01)

(58) Field of Classification Search
CPC .......... A61K 8/365; A61K 8/345; A61K 8/41; A61K 8/466; A61K 8/922; A61K 2800/4322; A61Q 5/10
USPC ............................................................ 8/405
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |

(Continued)

FOREIGN PATENT DOCUMENTS

| | | |
|---|---|---|
| CN | 106955248 A | 7/2017 |
| CN | 110193008 A | 9/2019 |

(Continued)

OTHER PUBLICATIONS

Non-Final Office Action in U.S. Appl. No. 17/853,722, mailed Jan. 8, 2024, 9 pages.

(Continued)

*Primary Examiner* — Eisa B Elhilo
(74) *Attorney, Agent, or Firm* — THE MARBURY LAW GROUP, PLLC

(57) ABSTRACT

The disclosure relates to compositions for altering the color of keratin fibers and methods of using the compositions. The compositions comprise (a) a bonding system comprising (i) at least one first bonding agent chosen from alpha-hydroxy acids comprising at least three hydrogen donor carboxyl groups and/or salts thereof; (ii) at least one second bonding agent chosen from glycine and/or salts thereof; and (iii) optionally, at least one third bonding agent chosen from amino sulfonic acids and/or salts thereof; (b) at least one fatty alcohol; (c) at least one fatty acid; (d) at least one alkyl polyglucoside; (e) at least one alkalizing agent; and (f) at least one solvent. The compositions can further comprise one or more oxidation dyes, couplers, oxidizing agents, or combinations thereof.

18 Claims, 1 Drawing Sheet

(56) References Cited

U.S. PATENT DOCUMENTS

| | | | |
|---|---|---|---|
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,288,770 A | 11/1966 | Butler | |
| 3,412,019 A | 11/1968 | Hoover et al. | |
| 3,472,840 A | 10/1969 | Stone et al. | |
| 3,589,978 A | 6/1971 | Kamal et al. | |
| 3,632,559 A | 1/1972 | Matter et al. | |
| 3,874,870 A | 4/1975 | Green et al. | |
| 3,917,817 A | 11/1975 | Vanlerberghe et al. | |
| 3,929,990 A | 12/1975 | Green et al. | |
| 3,966,904 A | 6/1976 | Green et al. | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Vanlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,133,957 A | 1/1979 | Riew | |
| 4,137,180 A | 1/1979 | Naik et al. | |
| 4,166,894 A | 9/1979 | Schaper | |
| 4,172,887 A | 10/1979 | Vanlerberghe et al. | |
| RE30,199 E | 1/1980 | Rose et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,362,528 A | 12/1982 | Grollier et al. | |
| 4,381,919 A | 5/1983 | Jacquet et al. | |
| 4,422,853 A | 12/1983 | Jacquet et al. | |
| 4,579,732 A | 4/1986 | Grollier et al. | |
| 4,591,610 A | 5/1986 | Grollier | |
| 4,608,250 A | 8/1986 | Jacquet et al. | |
| 4,761,273 A | 8/1988 | Grollier et al. | |
| 4,772,462 A | 9/1988 | Boothe et al. | |
| 4,777,040 A | 10/1988 | Grollier et al. | |
| 4,855,130 A | 8/1989 | Konrad et al. | |
| 4,874,554 A | 10/1989 | Lange et al. | |
| 4,948,579 A | 8/1990 | Jacquet et al. | |
| 4,970,066 A | 11/1990 | Grollier et al. | |
| 5,061,289 A | 10/1991 | Clausen et al. | |
| 5,196,189 A | 3/1993 | Jacquet et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 5,951,969 A | 9/1999 | Golinski et al. | |
| 5,985,803 A | 11/1999 | Rizvi et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,358,502 B1 | 3/2002 | Tanabe et al. | |
| 6,645,258 B2 | 11/2003 | Vidal et al. | |
| 6,730,789 B1 | 5/2004 | Birault et al. | |
| 7,507,261 B2 | 3/2009 | Nobuto et al. | |
| 8,236,063 B2 | 8/2012 | Reichert et al. | |
| 8,241,370 B2 | 8/2012 | Legrand et al. | |
| 9,095,518 B2 | 8/2015 | Pressly et al. | |
| 9,114,088 B2 | 8/2015 | Konno et al. | |
| 9,326,926 B2 | 5/2016 | Pressly et al. | |
| 9,597,273 B2 | 3/2017 | Pressly et al. | |
| 10,987,291 B2 | 4/2021 | Manneck et al. | |
| 11,160,739 B1 | 11/2021 | Shi et al. | |
| 11,337,906 B2 | 5/2022 | Lee et al. | |
| 11,559,474 B2 | 1/2023 | Degeorge et al. | |
| 11,596,588 B2 | 3/2023 | Machover et al. | |
| 11,857,660 B2 | 1/2024 | Shi et al. | |
| 2001/0052354 A1 | 12/2001 | Nishibe et al. | |
| 2002/0050013 A1 | 5/2002 | Vidal et al. | |
| 2003/0019051 A9 | 1/2003 | Vidal et al. | |
| 2004/0235700 A1 | 11/2004 | Legrand et al. | |
| 2006/0140887 A1 | 6/2006 | Molenda et al. | |
| 2007/0107142 A1 | 5/2007 | Nguyen et al. | |
| 2008/0317687 A1 | 12/2008 | Howe et al. | |
| 2010/0305064 A1 | 12/2010 | Walsh | |
| 2011/0150804 A1 | 6/2011 | Nojiri et al. | |
| 2012/0005843 A1* | 1/2012 | Benade | C07C 235/08 8/408 |
| 2012/0031423 A1 | 2/2012 | Wood et al. | |
| 2012/0048288 A1 | 3/2012 | Reichert et al. | |
| 2012/0114583 A1 | 5/2012 | Giesen et al. | |
| 2012/0329650 A1 | 12/2012 | Lopez-Cervantes | |
| 2013/0125914 A1 | 5/2013 | Battermann et al. | |
| 2013/0149274 A1 | 6/2013 | Nguyen et al. | |
| 2013/0156716 A1 | 6/2013 | Yontz | |
| 2014/0158150 A1 | 6/2014 | Schoepgens et al. | |
| 2014/0171354 A1 | 6/2014 | Miralles et al. | |
| 2014/0246041 A1 | 9/2014 | Krueger | |
| 2015/0004117 A1 | 1/2015 | Tan et al. | |
| 2015/0004119 A1 | 1/2015 | Tan et al. | |
| 2015/0034119 A1 | 2/2015 | Pressly et al. | |
| 2015/0037270 A1 | 2/2015 | Pressly et al. | |
| 2015/0037271 A1 | 2/2015 | Pressly et al. | |
| 2015/0202125 A1 | 7/2015 | Charrier et al. | |
| 2015/0202142 A1 | 7/2015 | Charrier et al. | |
| 2015/0283041 A1 | 10/2015 | Benn et al. | |
| 2015/0290101 A1 | 10/2015 | Pressly et al. | |
| 2015/0305469 A1 | 10/2015 | Paul | |
| 2015/0328102 A1 | 11/2015 | Pressly et al. | |
| 2016/0175238 A1 | 6/2016 | Shin et al. | |
| 2016/0235649 A1 | 8/2016 | Streuli | |
| 2017/0027832 A1 | 2/2017 | Wang | |
| 2017/0035667 A1 | 2/2017 | Benn et al. | |
| 2017/0246094 A1 | 8/2017 | Dreher et al. | |
| 2017/0273881 A1 | 9/2017 | Facheris et al. | |
| 2018/0021600 A1 | 1/2018 | Kobayashi et al. | |
| 2018/0042830 A1* | 2/2018 | Dreher | A61K 8/41 |
| 2018/0116930 A1 | 5/2018 | Degeorge et al. | |
| 2018/0116942 A1 | 5/2018 | Mahadeshwar et al. | |
| 2018/0177690 A1 | 6/2018 | Boulineau et al. | |
| 2018/0280286 A1 | 10/2018 | Elsen-Wahrer et al. | |
| 2018/0353404 A1 | 12/2018 | Nöcker et al. | |
| 2019/0125650 A1 | 5/2019 | Lee et al. | |
| 2019/0201309 A1* | 7/2019 | Machover | A61K 8/447 |
| 2021/0121385 A1 | 4/2021 | Muller et al. | |
| 2021/0154116 A1 | 5/2021 | Lee et al. | |
| 2021/0196600 A1 | 7/2021 | Shi et al. | |
| 2021/0196606 A1 | 7/2021 | Shi et al. | |
| 2021/0346261 A1 | 11/2021 | DeGeorge et al. | |
| 2022/0062142 A1 | 3/2022 | Henry | |
| 2023/0025989 A1 | 1/2023 | Shi | |
| 2023/0036005 A1 | 2/2023 | Shi | |
| 2023/0037788 A1 | 2/2023 | Shi et al. | |

FOREIGN PATENT DOCUMENTS

| | | |
|---|---|---|
| DE | 1220969 B | 7/1966 |
| DE | 2359399 A1 | 6/1975 |
| DE | 3843892 A1 | 6/1990 |
| DE | 4133957 A1 | 4/1993 |
| DE | 19543988 A1 | 5/1997 |
| DE | 102009028593 A1 | 2/2011 |
| EP | 0080976 A1 | 6/1983 |
| EP | 0122324 A1 | 10/1984 |
| EP | 0714954 A2 | 6/1996 |
| EP | 0770375 A1 | 5/1997 |
| EP | 1810657 A1 | 7/2007 |
| EP | 2123250 A1 | 11/2009 |
| EP | 2301520 A2 | 3/2011 |
| EP | 2460511 A1 | 6/2012 |
| FR | 1492597 A | 8/1967 |
| FR | 1583363 A | 10/1969 |

(56) References Cited

FOREIGN PATENT DOCUMENTS

| | | |
|---|---|---|
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2801308 A1 | 5/2001 |
| FR | 2886136 A1 | 12/2006 |
| FR | 2994088 A1 | 2/2014 |
| GB | 1026978 A | 4/1966 |
| GB | 1153196 A | 5/1969 |
| GB | 1546809 A | 5/1979 |
| JP | 63-154611 A | 6/1988 |
| JP | 02-019576 A | 1/1990 |
| JP | 05-163124 A | 6/1993 |
| JP | 08-198732 A | 8/1996 |
| JP | 2003-146844 A | 5/2003 |
| JP | 2005-029486 A | 2/2005 |
| JP | 2005-255534 A | 9/2005 |
| JP | 2015-086211 A | 5/2015 |
| KR | 10-2001-0039848 A | 5/2001 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 01/52005 A1 | 7/2001 |
| WO | 2006/066674 A1 | 6/2006 |
| WO | 2006/106390 A2 | 10/2006 |
| WO | 2006/134051 A1 | 12/2006 |
| WO | 2012/157657 A1 | 11/2012 |
| WO | 2013075892 A2 | 5/2013 |
| WO | 2013/136480 A1 | 9/2013 |
| WO | 2014/020148 A1 | 2/2014 |
| WO | 2014/020167 A2 | 2/2014 |
| WO | 2017/091796 A1 | 6/2017 |
| WO | 2017/207629 A1 | 12/2017 |
| WO | 2018/081399 A1 | 5/2018 |
| WO | 2018/183933 A1 | 10/2018 |
| WO | 2018/213652 A1 | 11/2018 |
| WO | 2019/133785 A1 | 7/2019 |
| WO | 2020/109859 A1 | 6/2020 |
| WO | 2021/138257 A1 | 7/2021 |
| WO | 2021138258 A1 | 7/2021 |

OTHER PUBLICATIONS

Porter, M.R., "Handbook of Surfactants," published by Blackie & Son (Glasgow and London), 1991, pp. 116-178.
International Search Report and Written Opinion for counterpart Application No. PCT/US2020/067153, dated Apr. 29, 2021.
Third-Party Submission Under 37 C.F.R. 1.290 for U.S. Appl. No. 17/133,376, filed Jan. 27, 2022 with exhibits.
International Search Report for counterpart Application No. PCT/US2020/067155, dated May 3, 2021.
International Search Report and Written Opinion for counterpart Application No. PCT/US2021/39047, dated Nov. 2, 2021.
Mintel: "One-Touch Color," Hoyu, XP55820021, Record ID 4957439, dated Jul. 13, 2017.
French Search Report and Written Opinion for counterpart French Application No. 2109798, dated Jun. 7, 2022.
Mintel: "Whipped Hair Color," Hoyu, Record ID 7277945, XP05592777, Feb. 20, 2020.
Mintel: "Beard Color," Hoyu Indonesia, Record No. 8923967, XP055927764, Aug. 16, 2001.
Mintel: "Speedy Color Quick Hair Colourant for Men," Hoyu, Record No. 3774805, XP055927781, Feb. 4, 2016.
French Search Report and Written Opinion for counterpart French Application No. 2109796, dated Jun. 3, 2022.
Third-Party Submission Under 37 C.F.R. 1.290 for U.S. Appl. No. 17/132,697, dated Jan. 27, 2022.
International Preliminary Report on Patentability for counterpart Application No. PCT/US2020/067155, dated Jul. 14, 2022.
International Preliminary Report on Patentability for counterpart Application No. PCT/US2020/067153, dated Jul. 14, 2022.
French Search Report and Written Opinion for counterpart Application No. FR 2110537, dated Jun. 27, 2022.
Non-Final Office Action for copending U.S. Appl. No. 17/101,206, dated Aug. 26, 2022.
Non-Final Office Action for copending U.S. Appl. No. 17/133,376, dated Sep. 20, 2022.
Non-Final Office Action for copending U.S. Appl. No. 17/132,697, dated Sep. 20, 2022.
First Examination Report for counterpart Indian Application No. 202217038673, dated Dec. 7, 2022.
First Examination Report for counterpart Indian Application No. 202217039846, dated Dec. 8, 2022.
Final Office Action for copending U.S. Appl. No. 17/133,376, dated Apr. 5, 2023.
Third Party Submission Under 37 CFR 1.290 for copending U.S. Appl. No. 17/132,697, (references only), dated Apr. 9, 2023.
International Search Report and Written Opinion for counterpart Application No. PCT/US2017/058495, dated Jan. 5, 2018.
Non-Final Office Action for copending U.S. Appl. No. 15/339,035, dated Jan. 10, 2018.
Non-Final Office Action for copending U.S. Appl. No. 15/339,035, dated Oct. 5, 2018.
Final Office Action for copending U.S. Appl. No. 15/339,035, dated May 2, 2019.
Non-Final Office Action for copending U.S. Appl. No. 15/339,035 dated Aug. 20, 2019.
Final Office Action for copending U.S. Appl. No. 15/339,035, dated Apr. 10, 2020.
Non-Final Office Action for copending U.S. Appl. No. 15/339,035, dated Jun. 25, 2021.
Final Office Action for copending U.S. Appl. No. 15/339,035, dated Apr. 14, 2022.
Non-Final Office Action for copending U.S. Appl. No. 15/339,035, dated Oct. 27, 2022.
International Preliminary Report on Patentability for counterpart Application No. PCT/US2017/058495, mailed May 9, 2019.
Olaplex with relaxers, OLAPLEX™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.
"Final Written Decision for U.S. Pat. No. 9,668,954 B2," Paper 78, Jul. 30, 2019, Case PGR2018-00025.
Non-Final Office Action for copending U.S. Appl. No. 15/801,425, mailed May 6, 2019.
Final Office Action for copending U.S. Appl. No. 15/801,425, mailed Nov. 12, 2019.
Non-Final Office Action for copending U.S. Appl. No. 15/801,425, mailed Jul. 24, 2020.
Third Party Submission for U.S. Appl. No. 17/379,405, dated May 10, 2022.
U.S. Appl. No. 61/994,709 "Hair Treatment Compositions and Methods," Inventors Pressly et al., May 16, 2014.
Final Office Action for copending U.S. Appl. No. 15/801,425, dated Feb. 26, 2021.
Non-Final Office Action for copending U.S. Appl. No. 15/801,425, dated Sep. 7, 2021.
Final Office Action for copending U.S. Appl. No. 15/801,425, dated May 31, 2022.
International Search Report and Written Opinion for counterpart Application No. PCT/US2021/047821, dated Feb. 7, 2022.
Database GNPD, "Oil Control Amino Acid Shampoo," Record ID No. 7915997, Mintel.
Database GNPD, "Illuminator Soap with Vitamin C," Record ID No. 4406687, Mintel.

(56) References Cited

OTHER PUBLICATIONS

Database GNPD, Anti Hair-Fall Fortifying Serum, Record ID No. 7242637, Mintel.
Database GNPD, "Elixium Plumping Anti-Aging Serumn," Record ID No. 6282723, Mintel.
Non-Final Office Action for copending U.S. Appl. No. 17/003,558, dated Jun. 23, 2022.
Non-Final Office Action for copending U.S. Appl. No. 17/003,558, dated Aug. 8, 2022.
International Preliminary Report on Patentability for counterpart Application No. PCT/US2021/047821, dated Feb. 28, 2023.
Non-Final Office Action for copending U.S. Appl. No. 17/379,405, dated Mar. 2, 2023.
Co-pending U.S. Appl. No. 17/878,001, entitled "Compositions and Methods for Altering the Color of Hair," Inventor: Shahid Nasser, filed Jul. 31, 2022.
French Search Report and Written Opinion for counterpart French Application No. FR2209427, dated Apr. 28, 2023.
Mintel: "Care & Moisture Color Permanent Hair Colour," Schwarzkopf and Henkel, Record ID 8511329, XP093042655, dated Feb. 24, 2021.
Mintel: "Colour and Protect Permanent Colouration," Schwarzkopf and Henkel, Record ID 8501329, XP093042658, dated Feb. 18, 2021.
Final Office Action for copending U.S. Appl. No. 17/101,206, dated May 26, 2023.
Final Office Action for copending U.S. Appl. No. 17/333,376, dated Apr. 5, 2023.
Final Office Action for copending U.S. Appl. No. 17/003,558, dated Jun. 26, 2023.
Co-pending U.S. Appl. No. 18/228,176, entitled "Compositions and Methods for Altering the Color of Hair," Inventors: Shahid Naseer et al., filed Jul. 31, 2023.
French Search Report and Written Opinion for counterpart French Application No. 2209666, dated May 9, 2023.
International Search Report and Written Opinion for counterpart Application No. PCT/US2023/029085, dated Oct. 19, 2023.
Non-Final Office Action for copending U.S. Appl. No. 17/853,663, dated Nov. 13, 2023.
Non-Final Office Action for copending U.S. Appl. No. 17/853,685, dated Aug. 10, 2023.
Final Office Action for copending U.S. Appl. No. 17/379,405, dated Sep. 18, 2023.
Non-Final Office Action for copending U.S. Appl. No. 17/003,558, dated Oct. 13, 2023.
International Preliminary Report on Patentability in PCT/US2022/035765, mailed Dec. 14, 2023, 8 pages.
Office Action in EP22747220.6, mailed Feb. 6, 2024, 3 pages.
Non-Final Office Action for copending U.S. Appl. No. 15/339,035, dated Apr. 22, 2024.
Non-Final Office Action for copending U.S. Appl. No. 17/101,206, dated Apr. 23, 2024.
Office Action in U.S. Appl. No. 17/878,001, mailed Feb. 20, 2024, 7 pages.
Office Action in CN202080090709.9, mailed Feb. 27, 2024, 10 pages.
Office Action in U.S. Appl. No. 17/003,558, mailed Mar. 25, 2024, 16 pages.
Non-Final Office Action for copendin U.S. Appl. No. 17/379,405, dated Mar. 1, 2024.

\* cited by examiner

COMPOSITIONS AND METHODS FOR ALTERING THE COLOR OF HAIR

TECHNICAL FIELD

The present disclosure relates to compositions for altering the color of hair and methods of using the compositions for altering the color of the hair, while at the same time enhancing fiber integrity of the hair.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair.

The process of altering the color of hair, for example, may involve lifting the color of the hair and/or depositing an artificial color onto the hair, which provides a different shade or color to the hair. The process of lifting the color of hair, also known as lightening, generally requires the use of compositions that comprise at least one oxidizing agent. Such oxidizing agents enter the hair shaft and react with melanin in the hair, thereby lightening the color of the hair. Additional agents, such as persulfate salts, may be added to accelerate the process.

Imparting a color change or color effect on hair can be done using permanent, demi-permanent, semi-permanent, or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents.

On the other hand, semi-permanent or temporary hair dyeing compositions typically use pigments, liposoluble dyes, or direct dyes chosen from acidic (anionic), basic (cationic), or neutral direct dyes which are deposited onto the hair fiber to impart color to the hair. Direct dyes are nonionic or ionic dyes and colored compounds capable of producing a more or less pronounced change of the natural color of the hair, resistant to shampoo-washing several times. These dyes may or may not be used in the presence of an oxidizing agent. In contrast with oxidation dye precursors, a direct dye is a relatively voluminous molecule that does not penetrate easily into the core of the fiber.

Hair lightening or color lifting compositions and hair dyeing compositions possess an alkalinity such that these compositions have a pH value of above 7, typically 9 and above, and may generally require the presence of ammonia or an ammonia gas-generating compound, or other alkalizing agents such as monoethanolamine (MEA) in amounts sufficient to make such compositions alkaline. These alkalizing agents cause the hair shaft to swell, helps open up the cuticle, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

While such compositions can effectively alter the color of hair, these chemical treatments with the use of these compositions are harsh and can cause damage to the hair fibers and decrease the strength of the hair, and may also negatively affect the sensorial properties, such as the smoothness, shine, and feel, of the hair. Additionally, hair that is damaged during a bleaching and/or dyeing process may not take up color satisfactorily, resulting in unevenness or non-uniformity of color.

Thus, in order to reduce or avoid these drawbacks of products and processes for altering the color of the hair as described above, new and additional ingredients and novel combinations of ingredients that can help prevent, ameliorate, or reverse damage before, during, or after, or as a complement to, processes for altering the color of the hair are continuously sought. Nevertheless, the choice of ingredients or combinations of ingredients could pose difficulties insofar as they cannot be detrimental to other cosmetic attributes such as ease and uniformity of application, rheology or viscosity properties of the compositions, stability of the compositions, and/or color deposit and target shade formation, and they cannot result in more disadvantages such as increased damage or a less healthy look to the hair.

As such, there is a need for developing new and improved products that can be used for effectively altering the color of hair, while at the same time, maintaining or improving the integrity of hair during coloring the hair and avoiding or minimizing damage to the hair. The present disclosure addresses these concerns and needs and relates to hair color-altering compositions incorporated with bonding actives to maintain and/or enhance the integrity of chemically treated hair and/or damaged hair during altering the color of hair.

SUMMARY

The present disclosure relates to compositions for altering the color of keratin fibers, particularly human hair, that comprise a synergistic combination of various components, including a bonding system. The disclosure also relates to methods of using the compositions for altering the color of hair.

The bonding system disclosed here comprises a first bonding agent chosen from alpha-hydroxy acids comprising at least three hydrogen donor carboxyl groups and/or salts thereof; a second bonding agent chosen from glycine and/or salts thereof; and optionally, a third bonding agent chosen from amino sulfonic acids and/or salts thereof. In some embodiments, the weight ratio of the first bonding agent(s) to the second bonding agent(s) may be greater than 1:5 and/or less than 1:1. It has surprisingly and unexpectedly been found that the bonding system disclosed herein, when included in a composition for altering the color of hair, provides integrity to keratin fibers and strengthens the fibers, and thus minimizes and/or prevents damage to the hair that is typically caused by chemical treatments during lifting or coloring the hair.

In various embodiments, the hair color-altering base compositions according to the present disclosure comprise: (a) a bonding system comprising (i) at least one first bonding agent chosen from alpha-hydroxy acids comprising at least three hydrogen donor carboxyl groups and/or salts thereof, (ii) at least one second bonding agent chosen from glycine and/or salts thereof, and (iii) optionally, at least one third bonding agent chosen from amino sulfonic acids and/or salts thereof; (b) at least one fatty alcohol; (c) at least one fatty acid; (d) at least one alkyl polyglucoside; (e) at least one alkalizing agent; and (f) at least one solvent comprising water. The pH of the hair color-altering base composition is typically greater than 7, such as from about 9 to about 11, from about 9.5 to about 11, or from about 9.5 to about 10.5. In some embodiments, the hair color-altering base compositions may further include one or more hair color-altering agents chosen from oxidation bases, couplers, or combinations thereof. In some further embodiments, the hair color-altering base compositions may comprise at least one vegetable oil. In some embodiments, the composition may further comprise at least one thickening agent. In yet further embodiments, the hair color-altering base compositions may include at least one polyol. The hair color-altering base compositions do not require cationic polymers, and thus may, in various embodiments, be free or essentially free of cationic polymers.

In various embodiments, the weight ratio of the first bonding agent(s) to the second bonding agent(s) in the base composition may be greater than 1:5 and less than 1:1, such as from about 1:1.1 to about 1:4.9, from about 1:1.5 to about 1:4.5, or from about 1:2 to about 1:4, or may be about 1:2.5. In a further exemplary and non-limiting embodiment, the bonding system disclosed herein includes citric acid, glycine, and optionally taurine, where the weight ratio of citric acid to glycine is greater than 1:5 and less than 1:1, such as from about 1:1.1 to about 1:4.9, from about 1:1.5 to about 1:4.5, or from about 1:2 to about 1:4, or may be about 1:2.5.

In some embodiments, the total amount of the first bonding agent(s) in the hair color-altering base composition typically ranges from about 0.1% to about 0.4% by weight, relative to the total weight of the base composition. In some embodiments, the total amount of the second bonding agent(s) in the hair color-altering base composition may be greater than 0.1% and less than 2% by weight, relative to the total weight of the base composition. In some embodiments, the total amount of the third bonding agent(s), if present, is greater than 0.1% and less than 2% by weight, relative to the total weight of the base composition.

In further embodiments, the fatty alcohol(s) may be chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, isotridecyl alcohol, cis-4-t-butylcyclohexanol, and myricyl alcohol, or mixtures thereof. The total amount of fatty alcohol(s) may range from about 0.5% to about 25% by weight, relative to the total weight of the base composition. In yet further embodiment, the at least one fatty acid may be present in an amount ranging from about 0.5% to about 15% by weight, relative to the total weight of the base composition, and may be chosen from myristic acid, lauric acid, palmitic acid, stearic acid, behenic acid, arichidonic acid, oleic acid, isostearic acid, sebacic acid, or a combination thereof.

In some embodiments, the total amount of alkyl polyglucoside(s) may range from about 0.05% to about 5% by weight, relative to the total weight of the composition. In some further embodiments, the at least one alkalizing agent may be chosen from organic alkalizing agents such as alkanolamines, mineral alkalizing agents such as ammonia or ammonium hydroxide, or combination thereof. In some embodiments, when alkanolamines are used, the total amount thereof may range from about 0.1% to about 10% by weight, relative to the total weight of the base composition. In some embodiments, when mineral alkalizing agents are used, the total amount thereof may range from about 0.1% to about 15% by weight, relative to the total weight of the base composition.

In some embodiments, the total amount of hair color-altering agents, when present, may range from about 0.0001% to about 10% by weight, relative to the total weight of the composition. In some embodiments, the amount of vegetable oil(s), when present, may range from about 0.5% to about 15% by weight, relative to the total weight of the base composition. In further embodiments, the total amount of thickening agent(s), when they are present, may range from about 0.05% to about 5% by weight, relative to the total weigh of the base composition. The thicken agent(s) may be chosen from polysaccharides chosen from celluloses, starches, gums, or mixtures thereof.

In some embodiments, the at least one polyol, when present, may be chosen from ethylene glycol, propylene glycol, butylene glycol, hexylene glycol, pentylene glycol, diethylene glycol, dipropylene glycol, 1,3 propanediol, glycerin, polyethylene glycols, or combinations thereof. The total amount of polyol(s), when present, is at least 0.5% by weight, relative to the total weight of the base composition.

In still further exemplary and non-limiting embodiments, the disclosure relates to a hair color-altering base composition comprising: (a) a bonding system comprising (i) a first bonding agent chosen from citric acid and/or salts thereof, in an amount ranging from about 0.1% to about 0.4%; (ii) a second bonding agent chosen from glycine and/or salts thereof, in an amount of greater than 0.1% and less than 2%; and (iii) optionally, a third bonding agent chosen from taurine and/or salts thereof, in an amount of greater than 0.1% and less than 2%; wherein the ratio of the total amount of first bonding agent(s) to the total amount of second bonding agent(s) is greater than 1:5 and less than 1:1; (b) at least one fatty alcohol; (c) at least one fatty acid; (d) at least one alkyl polyglucoside; (e) at least one alkalizing agent; (f) at least one color-altering agent chosen from oxidation dyes, couplers, or combinations thereof; (f) at least one solvent comprising water; (g) optionally, at least one vegetable oil, at least one thickening agent, and/or at least one polyol. The pH of the hair color-altering base composition is typically greater than 7, such as from about 9.5 to about 10.5. In some embodiments, the hair color-altering base composition does not include a cationic polymer.

In still further embodiments, the disclosure relates to a hair color-altering base composition comprising: (a) a bonding system comprising (i) at least one first bonding agent chosen from alpha-hydroxy acids comprising at least three hydrogen donor carboxyl groups and/or salts thereof, preferably chosen from citric acid, isocitric acid, aconitic acid, propane-1,2,3-tricarboxylic acid, benzene-1,3,5-tricarboxylic acid, agaric acid, trimesic acid, salts thereof, or combinations thereof, more preferably chosen from citric acid and/or salts thereof, wherein the total amount of first bonding agent(s) ranges from about 0.1% to about 0.4%, from about 0.1% to about 0.3%, from about 0.1% to about 0.25%, from about 0.1% to about 0.2%, from about 0.15% to about 0.4%, from about 0.15% to about 0.3%, from about 0.15% to about 0.25%, or from about 0.15% to about 0.2%, or is present in an amount of about 0.1%, about 0.15%, about 0.2%, about 0.25%, about 0.3%, about 0.35%, or about 4% by weight, relative to the total weight of the composition; (ii) at least one second bonding agent chosen from glycine and/or salts thereof, wherein the total amount of second bonding agent(s) present is greater than 0.1% and less than 2%, such as from about 0.15% to about 1.95%, from about 0.2% to about 1.75%, from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to about 0.6%, from about 0.2% to about 0.5%, from about 0.25% to about 1.5%, from about 0.25% to about 1.25%, from about 0.25% to about 1%, from about 0.25% to about 0.9%, from about 0.25% to about 0.8%, from about 0.25% to about 0.7%, from about 0.25% to about 0.6%, from about 0.25% to about 0.5%, from about 0.3% to about 1.5%, from about 0.3% to about 1.25%, from about 0.3% to about 1%, from about 0.3% to about 0.9%, from about 0.3% to about 0.8%, from about 0.3% to about 0.7%, from about 0.3% to about 0.6%, from about 0.3% to about 0.5%, from about 0.35% to about 1.5%, from about 0.35% to about 1.25%, from about 0.35% to about 1%, from about 0.35% to about 0.9%, from about 0.35% to about 0.8%, from about 0.35% to about 0.7%, from about 0.35% to about 0.6%, from about 0.35% to about 0.5%, from about 0.4% to about 1.5%, from about 0.4% to about 1.25%, from about 0.4% to about 1%, from about 0.4% to about 0.9%, from about 0.4% to about 0.8%, from about 0.4% to about 0.7%, from about 0.4% to about 0.6%, from about 0.4% to about 0.5%, from about 0.45% to about 1.5%, from about 0.45% to about 1.25%, from about 0.45% to about 1%, from about 0.45% to about 0.9%, from about 0.45% to about 0.8%, from about 0.45% to about 0.7%, from about 0.45% to about 0.6%, or from about 0.45% to about 0.5% by weight, relative to the total weight of the composition; and (iii) optionally at least one third bonding agent chosen from amino sulfonic acids and/or salts thereof, preferably chosen from aminomethane sulfonic acid, 2-aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, salts thereof, or mixtures thereof, more preferably chosen from taurine and/or salts thereof, wherein the total amount of third bonding agent(s) (if present) is greater than 0.1% and less than 2%, such as from about 0.2% to about 1.75%, from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to about 0.6%, from about 0.2% to about 0.5%, from about 0.25% to about 1.5%, from about 0.25% to about 1.25%, from about 0.25% to about 1%, from about 0.25% to about 0.9%, from about 0.25% to about 0.8%, from about 0.25% to about 0.7%, from about 0.25% to about 0.6%, from about 0.25% to about 0.5%, from about 0.3% to about 1.5%, from about 0.3% to about 1.25%, from about 0.3% to about 1%, from about 0.3% to about 0.9%, from about 0.3% to about 0.8%, from about 0.3% to about 0.7%, from about 0.3% to about 0.6%, from about 0.3% to about 0.5%, from about 0.35% to about 1.5%, from about 0.35% to about 1.25%, from about 0.35% to about 1%, from about 0.35% to about 0.9%, from about 0.35% to about 0.8%, from about 0.35% to about 0.7%, from about 0.35% to about 0.6%, from about 0.35% to about 0.5%, from about 0.4% to about 1.5%, from about 0.4% to about 1.25%, from about 0.4% to about 1%, from about 0.4% to about 0.9%, from about 0.4% to about 0.8%, from about 0.4% to about 0.7%, from about 0.4% to about 0.6%, from about 0.4% to about 0.5%, from about 0.45% to about 1.5%, from about 0.45% to about 1.25%, from about 0.45% to about 1%, from about 0.45% to about 0.9%, from about 0.45% to about 0.8%, from about 0.45% to about 0.7%, from about 0.45% to about 0.6%, or from about 0.45% to about 0.5% by weight, relative to the total weight of the composition; wherein the ratio of the total amount of first bonding agent(s) to the total amount of second bonding agent(s) is greater than 1:5 and less than 1:1, such as from about 1:1.1 to about 1:4.9, from about 1:1.25 to about 1:4.75, from about 1:2 to about 1:4, from about 1:2 to about 1:3.75, from about 1:2 to about 1:3.5, from about 1:2 to about 1:3.25, from about 1:2 to about 1:3; from about 1:2.25 to about 1:4, from about 1:2.25 to about 1:3.75, from about 1:2.25 to about 1:3.5, from about 1:2.25 to about 1:3.25; from about 1:2.5 to about 1:4, from 1:2.5 to about 1:3.75, from about 1:2.5 to about 1:3.5, or from about 1:2.5 to about 1:3.25; (b) at least one fatty alcohol; (c) at least one fatty acid; (d) at least one alkyl polyglucoside; (e) at least one alkalizing agent; (f) optionally at least one color-altering agent chosen from oxidation dyes, couplers, or combinations thereof; (f) at least one solvent comprising water; (g) optionally, at least one additional compound chosen from vegetable oils, thickening agents, and/or polyols, wherein the pH of the hair color-altering base composition is greater than 7, such as from about 9 to about 11, from about 9.5 to about 11, or from about 9.5 to about 10.5; wherein if a third bonding agent is present, the weight ratio of the second bonding agent(s) to the third bonding agent(s) optionally ranges from about 1:3 to about 3:1, such as from about 1:2.5 to about 2.5:1, from about 1:2 to about 2:1, from about 1:1.5 to about 1.5:1, from about 1:1.4 to about 1.4:1, from about 1:1.3 to about 1.3:1, from about 1:1.2 to about 1.2:1, from about 1:1.1 to about 1.1:1, or may be about 1:1; wherein if a third bonding agent is present, the weight ratio of the total amount of the first bonding agent(s) to the total combined amount of the second and third bonding agents is optionally greater than 1:10 but less than 1:1, such as ranging from 1:1 to about 1:8, from about 1:1 to about 1:6, from about 1:2 to about 1:10, from about 1:2 to about 1:8, from about 1:2 to about 1:6, from about 1:3 to about 1:10, from about 1:3 to about 1:8, from about 1:3 to about 1:6, from about 1:4 to about 1:10, from about 1:4 to about 1:8, from about 1:4 to about 1:6, or from about 1:4.5 to about 1:5.5, or is about 1:4, about 1:4.5, about 1:5, about 1:5.5, or about 1:6; and wherein the hair color-altering base composition is optionally free or essentially free of cationic polymers.

The hair color-altering base compositions disclosed herein are generally stable and can be stored at room temperature for at least 24 months. Any of the base compositions disclosed herein may be mixed, at the time or near the time of us, with a developer composition comprising at least one oxidizing agent to prepare a mixture, i.e., a hair color-altering composition, that can be applied on the hair for altering the color of the hair, while at the same time, maintaining or improving the integrity of the chemically treated hair and/or damaged hair.

The hair color-altering base compositions according to the disclosure are mixed with a developer composition comprising one or more oxidizing agents, at or near the time of use, to provide hair color-altering compositions according to the disclosure.

In yet further exemplary and non-limiting various embodiments, the disclosure relates to a method for altering the color of hair, including lifting the color or providing colors to hair, while imparting strength to the hair and minimizing or reducing damage to the hair by using the compositions disclosed herein. The method generally comprises applying a hair color-altering composition according to the present disclosure to the hair, and rinsing the composition off the hair after the composition is allowed to remain on the hair for a desired period of time ("leave-in time"), such as from about 1 minute to about 60 minutes. The hair color-altering composition is a mixture typically obtained at or near the time of use by mixing any of the hair color-altering base compositions disclosed herein with a developer composition comprising at least one oxidizing agent. The method thus may further comprise mixing any of the hair color-altering base compositions disclosed herein with the developer composition at or near the time of use to obtain the hair color-altering composition. The hair color-altering composition has a pH of greater than 7, such as from about 9 to about 11, or from about 9.5 to about 10.5. The hair may optionally be pre-bleached before the application of the color-altering compositions disclosed herein.

BRIEF DESCRIPTION OF THE FIGURE

The accompanying FIGURE, which is incorporated herein and constitutes part of this specification, illustrates exemplary embodiments of the disclosure, and, together with the general description given above and the description provided herein, serves to explain features of the disclosure.

Figure 1:
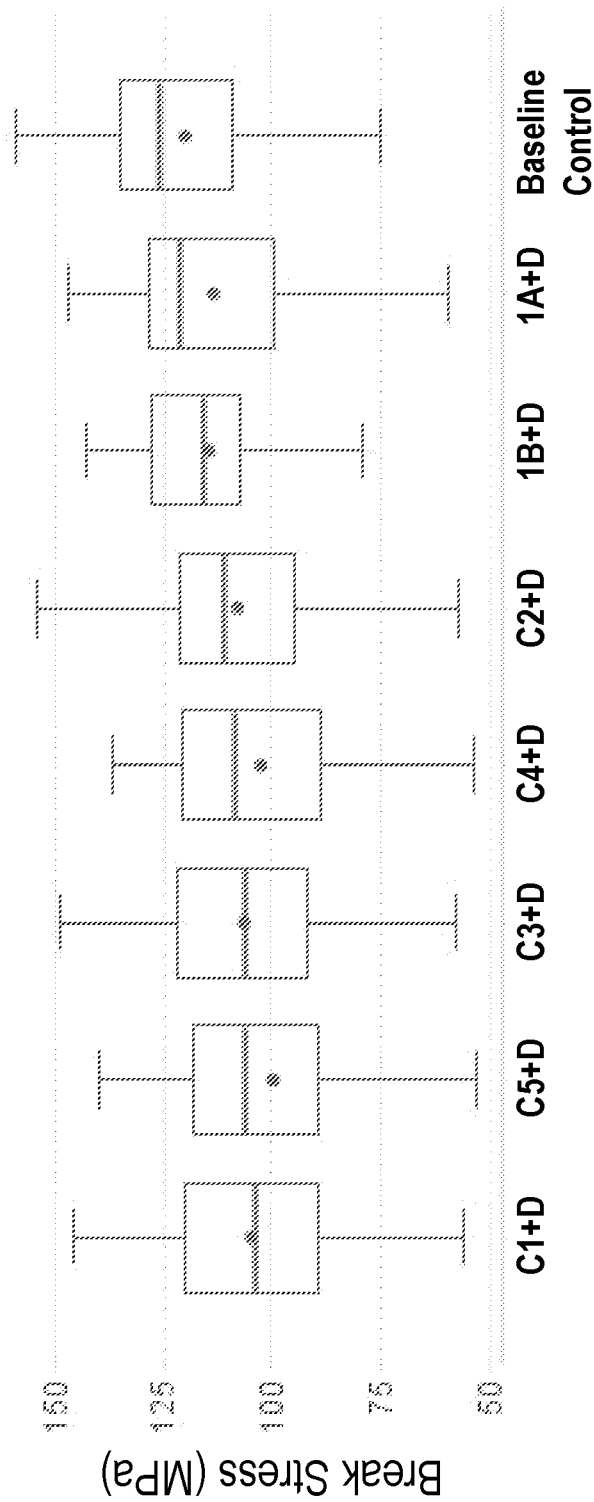
FIG. 1 is a graph illustrating the results of break stress of hair treated with compositions according to the disclosure in comparison with hair treated with comparative compositions and an untreated control.

It is to be understood that the foregoing and following descriptions are exemplary and explanatory only and are not intended to be restrictive of any subject matter claimed.

DETAILED DESCRIPTION

The present disclosure relates to compositions for altering the color of hair, as well as kits containing the compositions and methods of using the compositions. A unique feature of the compositions and methods according to the present disclosure is a bonding system incorporated in the compositions for altering the color of the hair, where the bonding system comprises a synergistic combination of one or more alpha-hydroxy acids comprising at least three hydrogen donor carboxyl groups and/or salts thereof, glycine and/or salts thereof, and optionally, one or more amino sulfonic acids and/or salts thereof. It has been surprisingly found that the synergistic combination can significantly enhance hair fiber integrity and/or minimize hair damage caused by chemical treatment.

I. Compositions

In various embodiments, the compositions according to the disclosure are compositions for altering the color of hair. Such hair color-altering compositions can be, in various embodiments, for demi-permanently or permanently altering the hair color. In each case, the compositions comprise a synergistic combination of (i) at least one first bonding agent chosen from one or more alpha-hydroxy acids comprising at least three hydrogen donor carboxyl groups and/or salts thereof; (ii) at least one second bonding agent chosen from glycine and/or salts thereof; and optionally (iii) at least one third bonding agent chosen from amino sulfonic acids and/or salts thereof. The compositions may be hair color-altering base compositions that can be mixed with a developer composition at or near the time of use, or may be a hair color-altering composition that is the mixture of a hair color-altering base composition and a developer composition comprising at least one oxidizing agent.

Hair Color-Altering Base Compositions

In various embodiments, a hair color-altering base composition (referred to interchangeably as "base compositions") according to the present disclosure comprises: (a) a bonding system comprising (i) at least one first bonding agent chosen from alpha-hydroxy acids comprising at least three hydrogen donor carboxyl groups and/or salts thereof, (ii) at least one second bonding agent chosen from glycine and/or salts thereof, and optionally (iii) at least one third bonding agent chosen from amino sulfonic acids and/or salts thereof; (b) at least one fatty alcohol; (c) at least one fatty acid; (d) at least one alkyl polyglucoside; (e) at least one alkalizing agent; and (f) at least one solvent. The weight ratio of the first bonding agent(s) to the second bonding agent(s) may optionally be greater than 1:5 and less than 1:1, such as from about 1:1.1 to about 1:4.9, from about 1:1.5 to about 1:4.5, or from about 1:2 to about 1:4, or may be about 1:2.5. In some embodiments, the hair color-altering base composition can further comprise one or more hair color-altering agents chosen from oxidation bases, couplers, or combinations thereof. In some embodiments, the hair color-altering base composition may further comprise at least one vegetable oil, at least one thickening agent, and/or at least one polyol. The hair color-altering base composition does not require cationic polymers and may be free or essentially free of cationic polymers. The pH of the hair color-altering base composition is typically greater than 7.

Bonding System

Hair color-altering base compositions according to the disclosure comprise a bonding system formed by a synergistic combination of: (i) at least one first bonding agent chosen from alpha-hydroxy acids comprising at least three hydrogen donor carboxyl groups and/or salts thereof; and (ii) at least one second bonding agent chosen from glycine and/or salts thereof. The amounts of the first bonding agent(s) and the second bonding agent(s) may be chosen such that a weight ratio of the first bonding agent(s) to the second bonding agent(s) is greater than 1:5 and less than 1:1, such as from about 1:1.1 to about 1:4.9, from about 1:1.5 to about 1:4.5, or from about 1:2 to about 1:4, or may be about 1:2.5. The bonding system may optionally further comprise (iii) at least one third bonding agent chosen from amino sulfonic acids and/or salts thereof.

In various embodiments, the at least one first bonding agent may be chosen from alpha-hydroxy acids comprising at least three hydrogen donor carboxyl groups (tricarboxylic acid), such as citric acid, isocitric acid, aconitic acid, propane-1,2,3-tricarboxylic acid, benzene-1,3,5-tricarboxylic acid, agaric acid, trimesic acid, salts thereof, or combinations thereof.

In various exemplary embodiments, the total amount of the first bonding agent(s) in the base compositions may range from about 0.1% to about 0.4% by weight, including all subranges therebetween, such as from about 0.1% to about 0.35%, from about 0.1% to about 0.3%, from about 0.1% to about 0.25%, from about 0.1% to about 0.2%, from about 0.1% to about 0.15%, from about 0.15% to about 0.4%, from about 0.15% to about 0.35%, from about 0.15% to about 0.3%, from about 0.15% to about 0.25%, from about 0.15% to about 0.2%, from about 0.2% to about 0.4%, from about 0.2% to about 0.35%, from about 0.2% to about 0.3%, from about 0.2% to about 0.25%, from about 0.25% to about 0.4%, from about 0.25% to about 0.35%, from about 0.25% to about 0.3%, from about 0.3% to about 0.4%, from about 0.3% to about 0.35%, or from about 0.35% to about 0.4% by weight, relative to the total weight of the composition. For example, the total amount of the first bonding agent(s) may be about 0.1%, about 0.15%, about 0.2%, about 0.25%, about 0.3%, about 0.35%, or about 4% by weight, relative to the total weight of the base composition.

In at least one embodiment, the first bonding agent comprises, consists essentially of, or consists of citric acid and/or salts thereof. For example, the base composition may comprise citric acid and/or salts thereof in an amount ranging from about 0.1% to about 0.4% by weight, including all aforementioned subranges, relative to the total weight of the base composition. As a further example, the base composition may comprise citric acid and/or salts thereof in an amount of about 0.1%, about 0.15%, about 0.2%, about 0.25%, about 0.3%, about 0.35%, or about 4% by weight, relative to the total weight of the base composition.

In various embodiments, compositions according to the present disclosure include at least one second bonding agent chosen from glycine and/or salt(s) thereof. In some embodiments, the total amount of glycine and/or salts thereof ranges from about 0.1% to about 2%, such as from about 0.2% to about 1.75% by weight, including all subranges therebetween, relative to the total weight of the base composition. For example, in various embodiments the total amount of glycine and/or salts thereof ranges from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to about 0.6%, from about 0.2% to about 0.5%, from about 0.2% to about 0.4%, from about 0.2% to about 0.3%, from about 0.25% to about 1.75%, from about 0.25% to about 1.5%, from about 0.25% to about 1.25%, from about 0.25% to about 1%, from about 0.25% to about 0.9%, from about 0.25% to about 0.8%, from about 0.25% to about 0.7%, from about 0.25% to about 0.6%, from about 0.25% to about 0.5%, from about 0.25% to about 0.4%, from about 0.25% to about 0.3%, from about 0.3% to about 1.75%, from about 0.3% to about 1.5%, from about 0.3% to about 1.25%, from about 0.3% to about 1%, from about 0.3% to about 0.9%, from about 0.3% to about 0.8%, from about 0.3% to about 0.7%, from about 0.3% to about 0.6%, from about 0.3% to about 0.5%, from about 0.3% to about 0.4%, from about 0.35% to about 1.75%, from about 0.35% to about 1.5%, from about 0.35% to about 1.25%, from about 0.35% to about 1%, from about 0.35% to about 0.9%, from about 0.35% to about 0.8%, from about 0.35% to about 0.7%, from about 0.35% to about 0.6%, from about 0.35% to about 0.5%, from about 0.35% to about 0.4%, from about 0.4% to about 1.75%, from about 0.4% to about 1.5%, from about 0.4% to about 1.25%, from about 0.4% to about 1%, from about 0.4% to about 0.9%, from about 0.4% to about 0.8%, from about 0.4% to about 0.7%, from about 0.4% to about 0.6%, from about 0.4% to about 0.5%, from about 0.45% to about 1.75%, from about 0.45% to about 1.5%, from about 0.45% to about 1.25%, from about 0.45% to about 1%, from about 0.45% to about 0.9%, from about 0.45% to about 0.8%, from about 0.45% to about 0.7%, from about 0.45% to about 0.6%, from about 0.45% to about 0.5%, from about 0.5% to about 1.75%, from about 0.5% to about 1.5%, from about 0.5% to about 1.25%, from about 0.5% to about 1%, from about 0.5% to about 0.9%, from about 0.5% to about 0.8%, from about 0.5% to about 0.7%, or from about 0.5% to about 0.6% by weight, relative to the total weight of the composition.

In some embodiments, the total amount of glycine and/or salts thereof is not less than exactly $0.\overline{20}\%$ by weight, relative to the total weight of the base composition. In some further embodiments, the total amount of glycine and/or salts thereof is not greater than exactly $1.\overline{99}\%$, such as not greater than exactly $1.9\overline{50}\%$, or not greater than exactly $1.\overline{90}\%$ by weight, relative to the total weight of the base composition. In further embodiments, the total amount of glycine and/or salts thereof is not greater than exactly $0.\overline{99}\%$, such as not greater than exactly $0.9\overline{5}\%$, or not greater than exactly $0.\overline{90}\%$ by weight, relative to the total weight of the base composition. In some embodiments, the total amount of glycine and/or salts thereof is not less than exactly $0.\overline{20}\%$, and not greater than exactly $1.\overline{99}\%$, such as not greater than exactly $1.9\overline{50}\%$, or not greater than exactly $1.\overline{90}\%$ by weight, relative to the total weight of the base composition. In some further embodiments, the total amount of glycine and/or salts thereof is not less than exactly $0.\overline{20}\%$, and not greater than exactly $0.\overline{99}\%$, such as not greater than exactly $0.9\overline{5}\%$, or not greater than exactly $0.\overline{90}\%$ by weight, relative to the total weight of the base composition. For example, in various embodiments, the total amount of glycine and/or salts thereof ranges from exactly $0.\overline{20}\%$ to exactly $1.\overline{99}\%$, from exactly $0.\overline{20}\%$ to exactly $1.9\overline{50}\%$, from exactly $0.\overline{20}\%$ to exactly $1.\overline{90}\%$, from exactly $0.\overline{20}\%$ to about 1.75%, from exactly $0.\overline{20}\%$ to about 1.5%, from exactly $0.\overline{20}\%$ to about 1%, from exactly $0.\overline{20}\%$ to about 0.9%, from exactly $0.\overline{20}\%$ to about 0.8%, from exactly $0.\overline{20}\%$ to about 0.7%, from exactly $0.\overline{20}\%$ to about 0.6%, from exactly $0.\overline{20}\%$ to about 0.5%, from exactly $0.\overline{20}\%$ to about 0.4%, or from exactly $0.\overline{20}\%$ to about 0.3% by weight, relative to the total weight of the base composition. In other embodiments, the total amount of glycine and/or salts thereof ranges from exactly $0.\overline{20}\%$ to exactly $0.\overline{99}\%$, from exactly $0.\overline{20}\%$ to exactly $0.9\overline{50}\%$, or from exactly $0.\overline{20}\%$ to exactly $0.\overline{90}\%$ by weight, relative to the total weight of the base composition. In still further embodiments, the total amount of glycine and/or salts thereof ranges from about 0.2% to exactly $1.\overline{99}\%$, from about 0.25% to exactly $1.\overline{99}\%$, from about 0.3% to exactly $1.\overline{99}\%$, from about 0.35% to exactly $1.\overline{99}\%$, from about 0.4% to exactly $1.\overline{99}\%$, from about 0.45% to exactly $1.\overline{99}\%$, from about 0.5% to exactly $1.\overline{99}\%$, from about 0.6% to exactly $1.\overline{99}\%$, from about 0.7% to exactly $1.\overline{99}\%$, from about 0.8% to exactly $1.\overline{99}\%$, from about 0.9% to exactly $1.\overline{99}\%$, from about 1% to exactly $1.\overline{99}\%$, from about 0.2% to exactly $1.9\overline{50}\%$, from about 0.25% to exactly $1.9\overline{50}\%$, from about 0.3% to exactly $1.9\overline{50}\%$, from about 0.35% to exactly $1.9\overline{50}\%$, from about 0.4% to exactly $1.9\overline{50}\%$, from about 0.45% to exactly $1.9\overline{50}\%$, from about 0.5% to exactly $1.9\overline{50}\%$, from about 0.6% to exactly $1.9\overline{50}\%$, from about 0.7% to exactly $1.9\overline{50}\%$, from about 0.8% to exactly $1.9\overline{50}\%$, from about 0.9% to exactly $1.9\overline{50}\%$, from about 1% to exactly $1.9\overline{50}\%$, from about 0.2% to exactly $1.\overline{90}\%$, from about 0.25% to exactly $1.\overline{90}\%$, from about 0.3% to exactly $1.\overline{90}\%$, from about 0.35% to exactly $1.\overline{90}\%$, from about 0.4% to exactly $1.\overline{90}\%$, from about 0.45% to exactly $1.\overline{90}\%$, from about 0.5% to exactly $1.\overline{90}\%$, from about 0.6% to exactly $1.\overline{90}\%$, from about 0.7% to exactly $1.\overline{90}\%$, from about 0.8% to exactly $1.\overline{90}\%$, from about 0.9% to exactly $1.\overline{90}\%$, from about 1% to exactly $1.\overline{90}\%$, from about 0.2% to exactly $0.\overline{99}\%$, from about 0.25% to exactly $0.\overline{99}\%$, from about 0.3% to exactly $0.\overline{99}\%$, from about 0.35% to exactly $0.\overline{99}\%$, from about 0.4% to exactly $0.\overline{99}\%$, from about 0.45% to exactly $0.\overline{99}\%$, from about 0.5% to exactly $0.\overline{99}\%$, from about 0.6% to exactly $0.\overline{99}\%$, from about 0.7% to exactly $0.\overline{99}\%$, from about 0.8% to exactly $0.\overline{99}\%$, from about 0.9% to exactly $0.\overline{99}\%$, from about 0.2% to exactly $0.9\overline{50}\%$, from about 0.25% to exactly $0.9\overline{50}\%$, from about 0.3% to exactly $0.9\overline{50}\%$, from about 0.35% to exactly $0.9\overline{50}\%$, from about 0.4% to exactly $0.9\overline{50}\%$, from about 0.45% to exactly $0.9\overline{50}\%$, from about 0.5% to exactly $0.9\overline{50}\%$, from about 0.6% to exactly $0.9\overline{50}\%$, from about 0.7% to exactly $0.9\overline{50}\%$, from about 0.8% to exactly $0.9\overline{50}\%$, from about 0.9% to exactly $0.9\overline{50}\%$, from about 0.2% to exactly $0.\overline{90}\%$, from about 0.25% to exactly $0.\overline{90}\%$, from about 0.3% to exactly 0.9$\overline{0}$%, from about 0.35% to exactly 0.9$\overline{0}$%, from about 0.4% to exactly 0.9$\overline{0}$%, from about 0.45% to exactly 0.9$\overline{0}$%, from about 0.5% to exactly 0.9$\overline{0}$%, from about 0.6% to exactly 0.9$\overline{0}$%, from about 0.7% to exactly 0.9$\overline{0}$%, from about 0.8% to exactly 0.9$\overline{0}$% by weight, relative to the total weight of the base composition.

In various embodiments, the amounts of the first bonding agent(s) and the second bonding agent(s) may be chosen such that the weight ratio of the first bonding agent(s) to the second bonding agent(s) allows the combination thereof to provide synergistic optimal fiber integrity benefit. In various embodiments of the disclosure, the first bonding agent(s) is typically included in an amount lesser than or equal to the amount of the second bonding agent(s), e.g. in a weight ratio of 1:1 or less. For instance, in certain embodiment, the weight ratio of the amount of the first bonding agent(s) to the amount of the second bonding agent(s) is greater than 1:5 but less than 1:1, including all subranges therebetween, such as ranging from about 1:1.001 to about 1:4.999, from about 1:1.1 to about 1:4.9, or from about 1:1.25 to about 1:4.75. In various exemplary embodiments, weight ratio of the amount of the first bonding agent(s) to the amount of the second bonding agent(s) may range from about 1:2 to about 1:4, from about 1:2 to about 1:3.75, from about 1:2 to about 1:3.5, from about 1:2 to about 1:3.25, from about 1:2 to about 1:3; from about 1:2.25 to about 1:4, from about 1:2.25 to about 1:3.75, from about 1:2.25 to about 1:3.5, from about 1:2.25 to about 1:3.25; from about 1:2.5 to about 1:4, from 1:2.5 to about 1:3.75, from about 1:2.5 to about 1:3.5, from about 1:2.5 to about 1:3.25. In some embodiments, the weight ratio of the first bonding agent(s) to the second bonding agent(s) is about 1:2, about 1:2.25, about 1:2.5, about 1:2.75, or about 1:3. In at least one embodiment, the base composition comprises citric acid and glycine, where the weight ratio of citric acid to glycine is about 1:2.5.

In some embodiments, base compositions according to the present disclosure may further include at least one third bonding agent chosen from amino sulfonic acids and salts thereof. Non-limiting examples of amino sulfonic acids include aminomethane sulfonic acid, 2-aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, and salts thereof. Combinations of at least two, such as at least three, at least four, etc., amino sulfonic acids and/or salts thereof are also contemplated.

If present, the total amount of the third bonding agent(s) may range from about 0.1% to about 2%, such as from about 0.2% to about 1.75% by weight, including all subranges therebetween, relative to the total weight of the base composition. For example, in various embodiments the total amount of the third bonding agent(s) ranges from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to about 0.6%, from about 0.2% to about 0.5%, from about 0.2% to about 0.4%, from about 0.2% to about 0.3%, from about 0.25% to about 1.75%, from about 0.25% to about 1.5%, from about 0.25% to about 1.25%, from about 0.25% to about 1%, from about 0.25% to about 0.9%, from about 0.25% to about 0.8%, from about 0.25% to about 0.7%, from about 0.25% to about 0.6%, from about 0.25% to about 0.5%, from about 0.25% to about 0.4%, from about 0.25% to about 0.3%, from about 0.3% to about 1.75%, from about 0.3% to about 1.5%, from about 0.3% to about 1.25%, from about 0.3% to about 1%, from about 0.3% to about 0.9%, from about 0.3% to about 0.8%, from about 0.3% to about 0.7%, from about 0.3% to about 0.6%, from about 0.3% to about 0.5%, from about 0.3% to about 0.4%, from about 0.35% to about 1.75%, from about 0.35% to about 1.5%, from about 0.35% to about 1.25%, from about 0.35% to about 1%, from about 0.35% to about 0.9%, from about 0.35% to about 0.8%, from about 0.35% to about 0.7%, from about 0.35% to about 0.6%, from about 0.35% to about 0.5%, from about 0.35% to about 0.4%, from about 0.4% to about 1.75%, from about 0.4% to about 1.5%, from about 0.4% to about 1.25%, from about 0.4% to about 1%, from about 0.4% to about 0.9%, from about 0.4% to about 0.8%, from about 0.4% to about 0.7%, from about 0.4% to about 0.6%, from about 0.4% to about 0.5%, from about 0.45% to about 1.75%, from about 0.45% to about 1.5%, from about 0.45% to about 1.25%, from about 0.45% to about 1%, from about 0.45% to about 0.9%, from about 0.45% to about 0.8%, from about 0.45% to about 0.7%, from about 0.45% to about 0.6%, from about 0.45% to about 0.5%, from about 0.5% to about 1.75%, from about 0.5% to about 1.5%, from about 0.5% to about 1.25%, from about 0.5% to about 1%, from about 0.5% to about 0.9%, from about 0.5% to about 0.8%, from about 0.5% to about 0.7%, or from about 0.5% to about 0.6% by weight, relative to the total weight of the composition.

In some embodiments, the total amount of the third bonding agent(s) is not less than exactly 0.2$\overline{0}$% by weight, relative to the total weight of the base composition. In some further embodiments, the total amount of the third bonding agent(s) is not greater than exactly 1.9$\overline{9}$%, such as not greater than exactly 1.95$\overline{0}$%, or not greater than exactly 1.9$\overline{0}$% by weight, relative to the total weight of the base composition. In further embodiments, the total amount of the third bonding agent(s) is not greater than exactly 0.9$\overline{9}$%, such as not greater than exactly 0.9$\overline{5}$%, or not greater than exactly 0.9$\overline{0}$% by weight, relative to the total weight of the base composition. In some embodiments, the total amount of the third bonding agent(s) is not less than exactly 0.2$\overline{0}$%, and not greater than exactly 1.9$\overline{9}$%, such as not greater than exactly 1.95$\overline{0}$%, or not greater than exactly 1.9$\overline{0}$% by weight, relative to the total weight of the base composition. In some further embodiments, the total amount of the third bonding agent(s) is not less than exactly 0.2$\overline{0}$%, and not greater than exactly 0.9$\overline{9}$%, such as not greater than exactly 0.9$\overline{5}$%, or not greater than exactly 0.9$\overline{0}$% by weight, relative to the total weight of the base composition. For example, in various embodiments, the total amount of the third bonding agent(s) ranges from exactly 0.2$\overline{0}$% to exactly 1.9$\overline{9}$%, from exactly 0.2$\overline{0}$% to exactly 1.95$\overline{0}$%, from exactly 0.2$\overline{0}$% to exactly 1.9$\overline{0}$%, from exactly 0.2$\overline{0}$% to about 1.75%, from exactly 0.2$\overline{0}$% to about 1.5%, from exactly 0.2$\overline{0}$% to about 1%, from exactly 0.2$\overline{0}$% to about 0.9%, from exactly 0.2$\overline{0}$% to about 0.8%, from exactly 0.2$\overline{0}$% to about 0.7%, from exactly 0.2$\overline{0}$% to about 0.6%, from exactly 0.2$\overline{0}$% to about 0.5%, from exactly 0.2$\overline{0}$% to about 0.4%, or from exactly 0.2$\overline{0}$% to about 0.3% by weight, relative to the total weight of the base composition. In other embodiments, the total amount of the third bonding agent(s) ranges from exactly 0.2$\overline{0}$% to exactly 0.9$\overline{9}$%, from exactly 0.2$\overline{0}$% to exactly 0.95$\overline{0}$%, or from exactly 0.2$\overline{0}$% to exactly 0.9$\overline{0}$% by weight, relative to the total weight of the base composition. In still further embodiments, the total amount of the third bonding agent(s) ranges from about 0.2% to exactly 1.9$\overline{9}$%, from about 0.25% to exactly 1.9$\overline{9}$%, from about 0.3% to exactly 1.9$\overline{9}$%, from about 0.35% to exactly 1.9$\overline{9}$%, from about 0.4% to exactly 1.9$\overline{9}$%, from about 0.45% to exactly 1.9$\overline{9}$%, from about 0.5% to exactly 1.9$\overline{9}$%, from about 0.6% to exactly 1.9$\overline{9}$%, from about 0.7% to exactly 1.9$\overline{9}$%, from about 0.8% to exactly 1.9$\overline{9}$%, from about 0.9% to exactly 1.9$\overline{9}$%, from about 1% to exactly 1.9$\overline{9}$%, from about 0.2% to exactly 1.95$\overline{0}$%, from about 0.25% to exactly 1.95$\overline{0}$%, from about 0.3% to exactly 1.95$\overline{0}$%, from about 0.35% to exactly 1.95$\overline{0}$%, from about 0.4% to exactly 1.95$\overline{0}$%, from about 0.45% to exactly 1.95$\overline{0}$%, from about 0.5% to exactly 1.95$\overline{0}$%, from about 0.6% to exactly 1.95$\overline{0}$%, from about 0.7% to exactly 1.95$\overline{0}$%, from about 0.8% to exactly 1.95$\overline{0}$%, from about 0.9% to exactly 1.95$\overline{0}$%, from about 1% to exactly 1.95$\overline{0}$%, from about 0.2% to exactly 1.9$\overline{0}$%, from about 0.25% to exactly 1.9$\overline{0}$%, from about 0.3% to exactly 1.9$\overline{0}$%, from about 0.35% to exactly 1.9$\overline{0}$%, from about 0.4% to exactly 1.9$\overline{0}$%, from about 0.45% to exactly 1.9$\overline{0}$%, from about 0.5% to exactly 1.9$\overline{0}$%, from about 0.6% to exactly 1.9$\overline{0}$%, from about 0.7% to exactly 1.9$\overline{0}$%, from about 0.8% to exactly 1.9$\overline{0}$%, from about 0.9% to exactly 1.9$\overline{9}$%, from about 1% to exactly 1.9$\overline{0}$%, from about 0.2% to exactly 0.9$\overline{9}$%, from about 0.25% to exactly 0.9$\overline{9}$%, from about 0.3% to exactly 0.9$\overline{9}$%, from about 0.35% to exactly 0.9$\overline{9}$%, from about 0.4% to exactly 0.9$\overline{9}$%, from about 0.45% to exactly 0.9$\overline{9}$%, from about 0.5% to exactly 0.9$\overline{9}$%, from about 0.6% to exactly 0.9$\overline{9}$%, from about 0.7% to exactly 0.9$\overline{9}$%, from about 0.8% to exactly 0.9$\overline{9}$%, from about 0.9% to exactly 0.9$\overline{9}$%, from about 0.2% to exactly 0.95$\overline{0}$%, from about 0.25% to exactly 0.95$\overline{0}$%, from about 0.3% to exactly 0.95$\overline{0}$%, from about 0.35% to exactly 0.95$\overline{0}$%, from about 0.4% to exactly 0.95$\overline{0}$%, from about 0.45% to exactly 0.95$\overline{0}$%, from about 0.5% to exactly 0.95$\overline{0}$%, from about 0.6% to exactly 0.95$\overline{0}$%, from about 0.7% to exactly 0.95$\overline{0}$%, from about 0.8% to exactly 0.95$\overline{0}$%, from about 0.9% to exactly 0.95$\overline{0}$%, from about 0.2% to exactly 0.9$\overline{0}$%, from about 0.25% to exactly 0.9$\overline{0}$%, from about 0.3% to exactly 0.9$\overline{0}$%, from about 0.35% to exactly 0.9$\overline{0}$%, from about 0.4% to exactly 0.9$\overline{0}$%, from about 0.45% to exactly 0.9$\overline{0}$%, from about 0.5% to exactly 0.9$\overline{0}$%, from about 0.6% to exactly 0.9$\overline{0}$%, from about 0.7% to exactly 0.9$\overline{0}$%, from about 0.8% to exactly 0.9$\overline{0}$% by weight, relative to the total weight of the base composition.

If at least one third bonding agent(s) is present, it may be particularly advantageous to include total amounts of second bonding agent(s) and third bonding agent(s) such that the weight ratio of the second bonding agent(s) to the third bonding agent(s) allows the combination thereof to increase the synergistic optimal fiber integrity benefit of the compositions. For example, the weight ratio of the second bonding agent(s) to the third bonding agent(s) may range from about 1:3 to about 3:1, such as from about 1:2.5 to about 2.5:1, from about 1:2 to about 2:1, from about 1:1.5 to about 1.5:1, from about 1:1.4 to about 1.4:1, from about 1:1.3 to about 1.3:1, from about 1:1.2 to about 1.2:1, from about 1:1.1 to about 1.1:1, or may be about 1:1. In at least one embodiment, the base composition comprises glycine and taurine, where the weight ratio of glycine to taurine is about 1:1.

If at least one third bonding agent is present, it may be particularly advantageous to include total amounts of first bonding agent(s), second bonding agent(s), and third bonding agent(s) such that the weight ratio of the first bonding agent(s) to the combined second and third bonding agents allows the combination thereof to provide synergistic optimal fiber integrity benefit. In various embodiments of the disclosure, the total amount of the first bonding agent(s) is typically less than or equal to the total combined amount of the second and third bonding agents, e.g. in a weight ratio of 1:1 or less, such as ranging from about 1:1 to about 1:10. For instance, in certain embodiments, the weight ratio of the total amount of the first bonding agent(s) to the total combined amount of the second and third bonding agents is greater than 1:10 but less than 1:1, including all subranges therebetween, such as from about 1:1 to about 1:9, from about 1:1 to about 1:8, from about 1:1 to about 1:7, from about 1:1 to about 1:6, from about 1:1 to about 1:5; from about 1:1 to about 1:4, from about 1:1 to about 1:3, from about 1:1 to about 1:2, from about 1:2 to about 1:10, from about 1:2 to about 1:9, from about 1:2 to about 1:8, from about 1:2 to about 1:7, from about 1:2 to about 1:6, from about 1:2 to about 1:5; from about 1:2 to about 1:4, from about 1:2 to about 1:3, from about 1:3 to about 1:10, from about 1:3 to about 1:9, from about 1:3 to about 1:8, from about 1:3 to about 1:7, from about 1:3 to about 1:6, from about 1:3 to about 1:5; from about 1:3 to about 1:4, from about 1:4 to about 1:10, from about 1:4 to about 1:9, from about 1:4 to about 1:8, from about 1:4 to about 1:7, from about 1:4 to about 1:6, or from about 1:4 to about 1:5. In some embodiments, the weight ratio of the first bonding agent(s) to the second bonding agent(s) is about 1:3, about 1:3.5, about 1:4, about 1:4.5, about 1:5, about 1:5.5, about 1:6, about 1:6.5, or about 1:7. In at least one embodiment, the base composition comprises citric acid, glycine, and taurine, where the weight ratio of citric acid to glycine+taurine (citric acid:[glycine+taurine]) is about 1:5.

Fatty Alcohols

Hair color-altering base compositions according to the disclosure comprise at least one fatty alcohol. Suitable fatty alcohols include those having a fatty group with a carbon chain of C5 or greater, such as, for example, from 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

In some embodiments, the fatty alcohol portion is optionally hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, or mixtures thereof. In some cases, the fatty alcohols may be chosen from myristyl alcohol, lauryl alcohol, cetyl alcohol, stearyl alcohol, cetearyl alcohol, isostearyl alcohol, oleyl alcohol, isotridecyl alcohol, or mixtures thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bonds), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols. As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater. Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, and C22-C24 pareth-33.

The total amount of fatty alcohol(s) can vary, but typically ranges from about 0.5% to about 25%, including all subranges therebetween, such as from about 0.5% to about 22%, from about 0.5% to about 20%, from about 0.5% to about 18%, from about 0.5% to about 15%, from about 0.5% to about 10%, from about 0.5% to about 8%, from about 1% to about 25%, from about 1% to about 22%, from about 1% to about 20%, from about 1% to about 18%, from about 1% to about 15%, from about 1% to about 10%, from about 2% to about 25%, from about 2% to about 22%, from about 2% to about 20%, from about 2% to about 18%, from about 2% to about 15%, from about 2% to about 10%, from about 3% to about 25%, from about 3% to about 22%, from about 3% to about 20%, from about 3% to about 18%, from about 3% to about 15%, from about 3% to about 10%, from about 5% to about 25%, from about 5% to about 22%, from about 5% to about 20%, from about 5% to about 18%, from about 5% to about 15%, from about 5% to about 10%, from about 10% to about 25%, from about 10% to about 22%, from about 10% to about 20%, from about 10% to about 18%, from about 10% to about 15%, from about 15% to about 25%, from about 15% to about 22%, from about 15% to about 20% by weight, relative to the total weight of the base composition.

In some embodiments, a hair color-altering base composition according to the present disclosure comprises at least two fatty alcohols, such as cetearyl alcohol and oleyl alcohol, wherein the total amount of the at least two fatty alcohols ranges from about 1% to about 25%, such as from about 10% to about 25% or from about 15% to about 20% by weight, relative to the total weight of the base composition.

Fatty Acids

Hair color-altering base compositions according to the disclosure comprise at least one fatty acid. Suitable fatty acids that can be included in the base compositions may have about 10 to about 30 carbon atoms, from about 12 to about 22 carbon atoms, or from about 16 to about 22 carbon atoms. These fatty acids can be straight or branched chain acids and can be saturated or unsaturated. Also included are diacids, triacids, and other multiple acids which meet the carbon number requirement herein. Further included herein are salts of these fatty acids. Nonlimiting examples of fatty acids include myristic acid, lauric acid, palmitic acid, stearic acid, behenic acid, arichidonic acid, oleic acid, isostearic acid, sebacic acid, or mixtures thereof. In some embodiments, the fatty acids may comprise myristic acid, palmitic acid, stearic acid, or mixtures thereof.

The amount of fatty acid(s) typically ranges from about 0.5% to about 15%, including all subranges therebetween, such as from about 0.5% to about 12%, from about 0.5% to about 10%, from about 0.5% to about 8%, from about 0.5% to about 6%, from about 0.5% to about 4%, from about 0.5% to about 3%, from about 1% to about 15%, from about 1% to about 12%, from about 1% to about 10%, from about 1% to about 8%, from about 1% to about 6%, from about 1% to about 4%, from about 2% to about 15%, from about 2% to about 12%, from about 2% to about 10%, from about 2% to about 8%, from about 2% to about 6%, from about 2% to about 4% by weight, relative to the total weight of the hair color-altering base composition.

In some embodiments, a hair color-altering base composition according to the present disclosure comprises oleic acid present in an amount ranging from about 2% to about 4% by weight, relative to the total weight of the base composition.

Vegetable Oils

In various embodiments, hair color-altering base compositions according to the disclosure may further comprise one or more vegetable oils. As used herein, the term "vegetable oils" refers to oils derived from a plant, for example, oils from seeds or fruits.

In some embodiments, suitable vegetable oils are chosen from hydrocarbon-based oils of plant origin and/or vegetable origin. Non-limiting examples of plant based or vegetable based oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

In some cases, the vegetable oils may be glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

In some instances, the vegetable oils may be essential oils. For example, the vegetable oil comprises may be chosen from sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang, or a mixture thereof.

In some embodiments, a hair color-altering base composition according to the present disclosure includes at least one oil chosen from saturated or unsaturated plant oils having less than 16 carbon atoms, for example, coconut oil, *Ricinus communis* (castor) seed oil, *Butyrospermum parkii* (shea) butter, palmitic acid, jojoba oil, or a mixture thereof.

The total amount of vegetable oils, if they are present, typically ranges from about 0.5% to about 10%, including all subranges therebetween, such as from about 0.5% to about 9%, from about 0.5% to about 8%, from about 0.5% to about 7%, from about 0.5% to about 6%, from about 0.5% to about 5%, from about 0.5% to about 4%, from about 1% to about 10%, from about 1% to about 9%, from about 1% to about 8%, from about 1% to about 7%, from about 1% to about 6%, from about 1% to about 5% by weight, based on the total weight of the base composition. In certain embodiments, the total amount of vegetable oil(s) is about 3%, about 4%, about 4.5%, about 5%, about 5.5%, about 6%, or about 7% by weight, relative to the total weight of the base composition. In an embodiment, a hair color-altering base composition disclosed herein comprises *Butyrospermum parkii* (shea) butter in an amount ranging from about 2% to about 10%, for example about 2% to about 8%, about 2% to about 6%, about 3% to about 5%, or about 4% by weight, relative to the total weight of the base composition.

In some embodiments, hair color-altering base compositions according to the disclosure may include synthetic oils and/or oils other than vegetable oils described above. When present, the total amount of synthetic oils and/or oils other than vegetable oils, may be about 5% or less, about 4% or less, about 3% or less, about 2% or less, about 1% or less, or about 0.5% or less by weight, based on the total weight of the base composition. In some embodiments, a hair color-altering base composition according to the present disclosure is free of or essentially free of synthetic oils and/or oils other than vegetable oils. In some cases, hair color-altering base compositions do not include oils other than vegetable oils.

Alkyl Polyglucosides

In various embodiments, hair color-altering base compositions according to the present disclosure comprise at least one alkyl polyglucoside. Suitable alkyl polyglucosides that may be included in the compositions include alkyl polyglucosides having the following formula (I):

$$R_1\text{—}O\text{—}(R_2O)_n\text{—}Z_{(x)} \qquad (I)$$

wherein:
  $R_1$ is an alkyl group having 8-18 carbon atoms;
  $R_2$ is an ethylene or propylene group;
  Z is a saccharide group with 5-6 carbon atoms;
  n is an integer ranging from 0 to 10; and
  x is an integer ranging from 1 to 5.

Non-limiting examples of alkyl polyglucosides include arachidyl glucoside, $C_{12\text{-}20}$ alkyl glucoside, caprylyl/capryl glucoside, cetearyl glucoside, coco-glucoside, lauryl glucoside, decyl glucoside, and sodium lauryl glucose carboxylate. In some cases, the alkyl polyglucoside compound is selected from the group consisting of cetearyl glucoside, lauryl glucoside, decyl glucoside, coco glucoside, and a mixture thereof. In at least one instance, the glucoside is cetearyl glucoside.

In various embodiments, the total amount of alkyl polyglucoside(s) in the ranges from about 0.01% to about 5%, including all subranges therebetween, such as from about 0.1% to about 5%, from about 0.1% to about 4.5%, from about 0.1% to about 4%, from about 0.1% to about 3.5%, from about 0.1% to about 3%, from about 0.1% to about 2.5%, from about 0.1% to about 2%, from about 0.1% to about 1.5%, from about 0.1% to about 1%, from about 0.2% to about 4.5%, from about 0.2% to about 4%, from about 0.2% to about 3.5%, from about 0.2% to about 3%, from about 0.2% to about 2.5%, from about 0.2% to about 2%, from about 0.2% to about 1.5%, from about 0.2% to about 1%, from about 0.2% to about 0.8%, from about 0.5% to about 4.5%, from about 0.5% to about 4%, from about 0.5% to about 3.5%, from about 0.5% to about 3%, from about 0.5% to about 2.5%, from about 0.5% to about 2%, from about 0.5% to about 1.5%, from about 0.5% to about 1% by weight, based on the total weight of the composition. In certain embodiments, the total amount of alkyl polyglucoside(s) is about 0.1%, about 0.2%, about 0.3%, about 0.4%, about 0.5%, about 0.6%, about 0.7%, about 0.8%, about 0.9%, or about 1% by weight, relative to the total weight of the base composition. In at least one embodiment, the compositions comprise from about 0.01% to about 3%, such as from about 0.1% to about 3%, from about 0.1% to about 2%, from about 0.1% to about 1%, or about 0.5% of cetearyl glucoside.

Alkalizing Agents

Hair color-altering base compositions according to the disclosure comprise at least one alkalizing agent. The alkalizing agents may be chosen from organic alkalizing agents and/or mineral alkalizing agents.

As non-limiting examples, suitable organic alkalizing agents may be chosen from alkanolamines. In various embodiment, suitable alkanolamines may be chosen from mono-, di- or trialkylamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof. In some embodiments, alkanolamine type that may be mentioned include but not limited to: monoethanolamine (also known as ethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane. In one embodiment, at least one alkalizing agent is chosen from alkanolamines, such as monoethanolamine. Optionally, the organic alkalizing agent may consist essentially of or consist of alkanolamines, or may consist essentially of or consist of monoethanolamine.

As non-limiting examples, suitable mineral alkalizing agents may be chosen from ammonia, ammonium carbonates, sodium carbonates, potassium carbonates, ammonium bicarbonates, sodium bicarbonates, potassium bicarbonates, ammonium hydroxides, sodium hydroxides, potassium hydroxides, salts thereof, hydrates thereof, or mixtures thereof. In some embodiments, the hair color-altering base compositions comprise ammonia and/or ammonium hydroxide. Optionally, the mineral alkalizing agent may consist essentially of or consist of ammonia and/or ammonium hydroxide.

In some embodiments, a hair color-altering base composition disclosed herein comprises at least one organic alkalizing agent and at least one mineral alkalizing agent. In some embodiments, the at least one alkalizing agent comprises, consists essentially of or consists of ammonia or ammonium hydroxide, alkanolamines, salts thereof, hydrates thereof, or combinations thereof. In at least one embodiment, a hair color-altering base composition disclosed herein comprises both monoethanolamine and ammonium hydroxide.

In some embodiments, alkalizing agents present in a hair color-altering base composition may be only chosen from organic alkalizing agents, and the hair color-altering base composition is free or substantially free of mineral alkalizing agents, such as ammonia and/or ammonium hydroxide. In this case, the base composition may comprise less than about 0.5%, less than about 0.4%, less than about 0.3%, less than about 0.2%, less than about 0.1%, or less than about 0.05% of mineral alkalizing agents. In certain embodiments, the hair color-altering base compositions disclosed herein comprise one or more organic alkalizing agents and are free or substantially free of ammonia and/or ammonium-based compounds.

In various embodiments, the amount of organic alkalizing agents may range from about 0.1% to about 10%, including all subranges therebetween, such as from about 0.1% to about 9%, from about 0.1% to about 8%, from about 0.1% to about 7%, from about 0.1% to about 6%, from about 0.1% to about 5%, from about 0.1% to about 4%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4% by weight, based on the total weight of the hair color-altering base composition.

As further examples, in some embodiments, the alkalizing agents may comprise at least one organic alkalizing agent and at least one mineral alkalizing agent, wherein the at least one organic alkalizing agent is present in an amount of at least 0.1%, such as from about 0.1% to about 10%, including all subranges therebetween, such as from about 0.3% to about 10%, from about 0.5% to about 10% by weight, relative to the total weight of the hair color-altering base composition; and the at least one mineral alkalizing agent is present in an amount ranging from about 0.1% to about 15%, such as from about 0.1% to about 10% by weight, relative to the total weight of the hair color-altering base composition.

In some non-limiting embodiments where the hair color-altering base composition comprises at least one organic alkalizing agent and at least one mineral alkalizing agent. For instance, in one embodiments, the hair color-altering base composition comprises monoethanolamine in combination with ammonia and/or ammonium hydroxide.

When both organic alkalizing agents and mineral alkalizing agents are present, the total amount of the alkalizing agents may range from about 1% to about 20%, including all subranges therebetween, such as from about 1.5% to about 18%, from about 2% to about 16%, from about 2.5% to about 15%, or from about 3% to about 14%, or from about 4% to about 13% by weight, relative to the total weight of the base composition, for example from about 1% to about 18%, from about 1% to about 16%, from about 1% to about 15%, from about 1% to about 14%, from about 1% to about 13%, from about 1% to about 12%, from about 1.5% to about 20%, from about 1.5% to about 16%, from about 1.5% to about 15%, from about 1.5% to about 14%, from about 1.5% to about 13%, from about 1.5% to about 12%, from about 2% to about 20%, from about 2% to about 18%, from about 2% to about 15%, from about 2% to about 14%, from about 2% to about 13%, from about 2% to about 12%, from about 2.5% to about 20%, from about 2.5% to about 18%, from about 2.5% to about 16%, from about 2.5% to about 14%, from about 2.5% to about 13%, from about 2.5% to about 12%, from about 3% to about 20%, from about 3% to about 18%, from about 3% to about 16%, from about 3% to about 15%, from about 3% to about 13%, from about 3% to about 12%, from about 4% to about 20%, from about 4% to about 18%, from about 4% to about 16%, from about 4% to about 15%, from about 4% to about 14%, or from about 4% to about 12% by weight, relative to the total weight of the base composition.

Hair Color-Altering Agents

Hair color-altering base compositions according to the present disclosure may optionally comprise one or more hair color-altering agents (hair colorants). The one or more hair color-altering agents are generally chosen from oxidation dyes, i.e., oxidation bases or oxidative dye precursors, optionally combined with one or more couplers.

In various embodiments, suitable oxidation dyes bases may be chosen from para-phenylenediamines, bis(phenyl) alkylenediamines, para-aminophenols, ortho-aminophenols and heterocyclic bases, the addition salts thereof, or combinations thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis((3-hydroxyethyl)-para-phenylenediamine, 4-N,N-bis(β-hydroxyethyl)amino-2-methylaniline, 4-N,N-bis(p-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N—(R-hydroxypropyl)-para-phenylenediamine, 2-hydroxymethyl-para-phenylenediamine, N,N-dimethyl-3-methyl-para-phenylenediamine, N-ethyl-N—(R-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-R-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly useful.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(R-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the meta-aminophenols, 3-aminophenol and salts thereof, may be mentioned.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-□-hydroxyethoxy-3-amino-pyrazolo[1,5-a]pyridine; 2-(4-diméthylpyperazinium-1-yl)-3-amino-pyrazolo[1,5-a]pyridine; and the addition salts thereof.

In certain embodiments, oxidation bases can be selected from 3-aminopyrazolo-[1,5-a]-pyridines, optionally substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more (C1-C6)alkyl, such as di(C1-C4)alkylpipérazinium; or
(c) one (C1-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375, or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)

amino-1-methylpyrazole, and the addition salts thereof. 4,5-Diamino-1-(β-methoxyethyl)pyrazole may also be used. A 4,5-diaminopyrazole may be used, for example 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof can be chosen.

4,5-Diamino-1-(β-hydroxyethyl)pyrazole and/or 2,3-diamino-6,7-dihydro-1H,5H-pyrazolo[1,2-a]pyrazol-1-one and/or a salt thereof can be used as heterocyclic bases.

Hair color-altering base compositions according to the disclosure may optionally comprise one or more couplers advantageously chosen from those conventionally used in dyeing or coloring of keratinous substrates. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(ß-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(ß-hydroxyethyloxy)benzene, 2-amino-4-(ß-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-ß-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(ß-hydroxyethyl)amino-3,4-methylenedioxybenzene, 2,6-bis(ß-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

In some embodiments, the base compositions disclosed herein include at least one oxidation base chosen from toluene-toluene-2,5-diamine, acid salts thereof, or solvates thereof. In one embodiment, the base compositions may include at least one coupler chosen 2,4-diaminophenoxyethanol, and derivatives thereof, addition salts thereof, solvates thereof, or solvates of salts thereof; meta-aminophenol (1-hydroxy-3-aminobenzene) and derivatives thereof, addition salts thereof, solvates thereof, or solvates of salts thereof; or mixtures thereof.

The oxidation base(s), when present, may individually or collectively be present in an amount ranging from about 0.0001% to about 10% by weight, including all subranges therebetween, such as such as from about 0.0001% to about 8%, from about 0.0001% to about 6%, from about 0.0001% to about 4%, from about 0.0001% to about 2%, from about 0.001% to about 10%, from about 0.001% to about 8%, from about 0.001% to about 6%, from about 0.001% to about 4%, from about 0.001% to about 2% by weight, from about 0.003% to about 10%, from about 0.003% to about 8%, from about 0.003% to about 6%, from about 0.003% to about 4%, from about 0.003% to about 2%, from about 0.005% to about 10%, from about 0.005% to about 8%, from about 0.005% to about 6%, from about 0.005% to about 4%, from about 0.005% to about 2% by weight, relative to the total weight of the base composition, including increments and ranges therein there between.

The coupler(s), when present, may individually or collectively be present in an amount ranging from about 0.0001% to about 10% by weight, including all subranges therebetween, such as from about such as from about 0.0001% to about 8%, from about 0.0001% to about 6%, from about 0.0001% to about 4%, from about 0.0001% to about 2%, from about 0.001% to about 10%, from about 0.001% to about 8%, from about 0.001% to about 6%, from about 0.001% to about 4%, from about 0.001% to about 2% by weight, from about 0.003% to about 10%, from about 0.003% to about 8%, from about 0.003% to about 6%, from about 0.003% to about 4%, from about 0.003% to about 2%, from about 0.005% to about 10%, from about 0.005% to about 8%, from about 0.005% to about 6%, from about 0.005% to about 4%, from about 0.005% to about 2% by weight, relative to the total weight of the base composition, including increments and ranges therein there between.

Solvents

Hair color-altering base compositions according to the disclosure comprise a cosmetically acceptable solvent. The solvent may comprise water, non-aqueous solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises one or more non-aqueous solvents, other than or in addition to ingredients discussed above. For example, C1-C4 alcohols, organic solvents, fatty alcohols, fatty ethers, fatty esters, polyols other than those described above, glycols, vegetable oils, mineral oils, liposomes, laminar lipid materials, or any a mixture thereof. Non-limiting examples of solvents which may be used include alkane polyols such as 1,2,6-hexanetriol, trimethylolpropane, ethylene glycol, propylene glycol, diethylene glycol, hexylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol (isopropyl alcohol); glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbitol, sorbitan, acetine, diacetine, triacetine, sulfolane, or mixtures thereof. At least in some embodiments, the compositions contain water and at least one, for example two or more, additional solvent chosen from caprylyl glycol, hexylene glycol, ethylhexylglycerin, glycerin, or mixtures thereof.

The solvent may be present in the base composition in an amount ranging from about 20% to about 90% by weight, relative to the total weight of the composition, including all ranges and subranges therebetween. For example, in one embodiment, the total amount of solvent may be about 20% to about 85%, about 25% to about 85%, about 30% to about 85%, about 40% to about 85%, about 45% to 85%, or about 50% to 80% by weight, relative to the total weight of the base composition.

In certain embodiments, the solvent is primarily comprised of water, such as from about 20% to about 85%, about 20% to about 80%, about 20% to about 75%, about 20% to about 70%, about 20% to about 60%, about 20% to about 50%, about 20% to about 40%; from about 25% to about 90%%, about 25% to about 85%, about 25% to about 80%, about 25% to about 75%, about 25% to about 70%, about 25% to about 60%, about 25% to about 50%, about 25% to about 40%; from about 30% to about 90%%, about 30% to about 85%, about 30% to about 80%, about 30% to about 75%, about 30% to about 70%, about 30% to about 60%, about 30% to about 50%; from about 35% to about 90%%, about 35% to about 85%, about 35% to about 80%, about 35% to about 75%, about 35% to about 70%, about 35% to about 60%, about 35% to about 50%; from 40% to about 90%%, about 40% to about 85%, about 40% to about 80%, about 40% to about 75%, about 40% to about 70%, or about 40% to about 60% by weight, relative to the total weight of the base composition.

Thickening Agents

In some embodiments, hair color-altering base compositions described herein may further include at least one thickening agent. "Thickening agents" as used here may be referred to as "thickeners" or "viscosity modifying agents." Thickening agents are typically included to increase the viscosity of the compositions. Nonetheless, in some instances, certain thickening agents provide additional, surprising benefits to the base compositions.

In some embodiments, thickening agents are water-soluble, and increase the viscosity of water or form an aqueous gel when ingredients according to the present disclosure are dispersed/dissolved in water to formulate the base compositions. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

As non-limiting examples, thickening agents may be chosen from xanthan gum, guar gum, biosaccharide gum, cellulose, acacia seneca gum, sclerotium gum, agarose, pectin, gellan gum, hyaluronic acid, or mixtures thereof. Additionally, the at least one thickening agent may include polymeric thickening agents chosen from ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, or mixtures thereof. In some cases, the composition may optionally include ammonium polyacryloyldimethyl taurate and/or sodium polyacrylate. Suitable thickening agents may be found, for example, in U.S. Pat. No. 11,337,906, which is incorporated herein by reference.

According to some embodiments, non-limiting examples of thickening agents may include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-C24 hydroxyl substituted aliphatic acid, C8-C24 conjugated aliphatic acid, sugar fatty esters, polyglyceryl esters, or mixtures thereof.

Exemplary thickening agents that may be mentioned include: (1) carboxylic acid or carboxylate based homopolymers or co-polymers, which can be linear or crosslinked; (2) celluloses; (3) polyvinylpyrrolidone (PVP) and co-polymers; (4) sucrose esters; (5) polyglyceryl esters; (6) gums; and mixtures thereof.

(1) Carboxylic Acid or Carboxylate Based Homopolymers or Co-Polymers, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, or mixtures thereof.

(2) Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, or mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is optionally hydroxypropylcellulose (HPC).

(3) Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer may be chosen.

(4) Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

(5) Polyglyceryl Esters:

Non-limiting polyglycerol esters of fatty acids (polygylceryl esters) include those of the following formula (II):

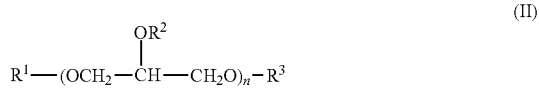

(II)

wherein n ranges from 2 to 20, from 2 to 10, or from 2 to 5, or is 2, 3, 4, 5, 6, 7, 8, 9, or 10, and $R^1$, $R^2$, and $R^3$ each may independently be chosen from fatty acid moieties or hydrogen, provided that at least one of $R^1$, $R^2$, and $R^3$ is a fatty acid moiety. For instance, $R^1$, $R^2$, and $R^3$ may be saturated or unsaturated, linear or branched, and have a length of C1-C40, C1-C30, C1-C25, or C1-C20, C1-C16, or C1-C10. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

(6) Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

In various embodiments, the total amount of thickening agents, when present in the hair color-altering base compositions, may range from about 0.01% to about 10% by weight, including all subranges therebetween, such as from about 0.01% to about 9%, from about 0.01% to about 8%, from about 0.01% to about 6%, from about 0.01% to about 4%, from about 0.01% to about 3%, from about 0.01% to about 2.5%, from about 0.01% to about 2%, from about 0.01% to about 1.5%, from about 0.01% to about 1%, from about 0.05% to about 10%, from about 0.05% to about 8%, from about 0.05% to about 6%, from about 0.05% to about 4%, from about 0.05% to about 3%, from about 0.05% to about 2.5%, from about 0.05% to about 2%, from about 0.05% to about 1.5%, from about 0.05% to about 1%, from about 0.1% to about 10%, from about 0.1% to about 8%, from about 0.1% to about 6%, from about 0.1% to about 4%, from about 0.1% to about 3%, from about 0.1% to about 2.5%, from about 0.1% to about 2%, from about 0.1% to about 1.5%, or from about 0.1% to about 1% by weight, based on the total weight of the base composition. For example, compositions according to the disclosure may comprise a total amount of thickener ranging from about 0.1% to about 0.9%, about 0.2% to about 0.8%, about 0.3% to about 0.7%, or about 0.4% to about 0.6% by weight, based on the total weight of the base composition.

Polyols

In some embodiments, hair color-altering base compositions according to the present disclosure may further comprise one or more polyols. In certain embodiments, the base compositions disclosed herein comprise at least two polyols. As used herein, the term "polyol" refers to an organic molecule comprising at least two free hydroxyl groups. The polyols may be liquid at ambient temperature (25° C.). Suitable polyols that may be comprised in the compositions disclosed herein may be glycols or compounds with numerous hydroxyl groups. In some cases, the at least on polyol is chosen from polyols having 2-32 carbon atoms, i.e., C2-C32 polyols, such as from 3 to 16 carbon atoms, or from 3 to 12 carbon atoms.

By way of example, the at least one polyol, when present, may be chosen from ethylene glycol, propylene glycol, butylene glycol, hexylene glycol, glycerin, diglycerin, diethylene glycol, and dipropylene glycol, polyethylene glycols, or mixtures thereof. In some cases, the compositions include propylene glycol. In some further cases, the compositions include one or both of propylene glycol and butylene glycol. Additionally, in some cases, the composition comprises propylene glycol, and optionally at least one polyol other than propylene glycol.

Non-limiting examples of polyols that may, optionally, be included in the compositions according to the present disclosure include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and/or a mixture thereof.

In some embodiments, the at least one polyol that is optionally included is chosen from glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol, or mixtures thereof. In some cases, a composition according to the present disclosure may include at least one polyol chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, or a mixture thereof.

If present, the amount of the at least one polyol may vary but typically ranges from about 0.1% to about 15%, including all subranges therebetween, such as from about 0.1% to about 15%, from about 0.1% to about 12%, from about 0.1% to about 10%, from about 0.1% to about 8%, from about 0.1% to about 5%, from about 0.1% to about 4%, from about 0.1% to about 3%, from about 0.1% to about 2%, from about 0.1% to about 1.5%, from about 0.1% to about 1%, from about 0.5% to about 15%, from about 0.5% to about 12%, from about 0.5% to about 10%, from about 0.5% to about 8%, from about 0.5% to about 5%, from about 0.5% to about 4%, from about 0.5% to about 3%, from about 0.5% to about 2%, from about 0.5% to about 1.5%, from about 0.5% to about 1%, from about 1% to about 15%, from about 1% to about 12%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 1.5% to about 15%, from about 1.5% to about 12%, from about 1.5% to about 10%, from about 1.5% to about 9%, from about 1.5% to about 8%, from about 1.5% to about 7%, from about 1.5% to about 6%, from about 1.5% to about 5%, from about 1.5% to about 4%, from about 1.5% to about 3%, or from about 1.5% to about 2% by weight, relative to the total weight of the composition. For example, the at least one polyol may be present in an amount ranging from about 1% to about 9%, such as about 1.5% to about 8.5% by weight, relative to the total weight of the composition.

Additional Components

Hair color-altering base compositions according to the disclosure may optionally comprise one or more additional components suitable for use in cosmetic compositions, and in particular suitable for altering the color of hair.

pH Adjusters

The hair color-altering base compositions may include one or more pH adjusters to increase or decrease the overall pH of the compositions. For example, one or more acids may be included to decrease the pH of the compositions. Examples of suitable acids for decreasing the pH of the compositions may include one or more acids, such as acetic acid and the like. The compositions may include one or more bases, such as sodium hydroxide, potassium hydroxide and the like, to increase the pH of the compositions to arrive at a desired pH value. Additional or alternative acids and bases that are suitable for adjusting the pH of the compositions are readily known to one of ordinary skill in the art.

The amount of the pH adjuster in the hair color-altering base compositions may be based on the desired pH of the final compositions and/or product. For example, the total amount of the pH adjuster may range from about 0.0001% to about 15%, based on the total weight of the composition. In some instances, the total amount of pH adjusters ranges from about 0.005% to about 10%, about 0.01% to about 5%, about 0.1% to about 1%, or about 0.1% to about 0.5% by weight, including ranges and sub-ranges therebetween, based on the total weight of the base composition. For instance, in one embodiment, the pH adjuster is about 0.1 M of sodium hydrate (NaOH).

Preservatives

One or more preservatives may be included in the hair color-altering compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldehyde, Chlorphenesin, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), or mixtures thereof. In some cases, the hair color-altering base compositions may include one or more preservatives selected from the group consisting of sodium benzoate, benzoic acid, chlorhexidine digluconate, chlorhexidine dihydrochloride, salicylic acid, phenoxyethanol, methyl paraben, or mixtures thereof.

The total amount of the one or more preservatives, when present, may vary. In some cases, the total amount of the one or more preservatives is about 0.01% to about 5%, about 0.01% to about 4%, about 0.15% to about 1%, or about 1% to about 3%, by weight, relative to the total weight of the base composition.

Auxiliary Components

Hair color-altering base compositions according to the disclosure may optionally comprise any auxiliary component suitable for use in such compositions. Such components may include, but are not limited to, dyes/pigments other than the dyes described above, for example, pearl pigments, mica, and titanium dioxide, rheology modifying agents such as acrylic polymers, surfactants, polymers, film forming agents or polymers, humectants and moisturizing agents, fatty substances other than the fatty alcohols, fatty acids, and oils described above, emulsifying agents other than fatty substances, fillers, structuring agents, propellants, shine agents, conditioning agents, antioxidants or reducing agents, penetrants, sequestrants, fragrances, buffers, dispersants, plant extracts, opacifiers, vitamins, conditioning agents, for instance volatile or non-volatile, modified or unmodified silicones, ceramides, preserving agents, opacifiers, sunscreen agents, and antistatic agents. As such, optional auxiliary components will be chosen so as to minimize any detrimental effect to the advantages of the hair color bases and compositions described herein.

Optional auxiliary components may be present in an amount ranging up to about 15%, such as from about 0.001% to about 10%, from about 0.01% to about 5%, or from about 0.1% to about 3% by weight, relative to the total weight of the hair color-altering base composition.

In various embodiments, hair color-altering base compositions according to the present disclosure have a pH of greater than 7, such as a pH ranging from about 7.5 to about 13, from about 8 to about 13, from about 8.5 to about 13, from about 9 to about 13, from about 9.5 to about 13, from about 10 to about 13, from about 8 to about 12, from about 8 to about 11, from about 8 to about 10.5, from about 9 to about 13, from about 9 to about 12, from about 9 to about 11, from about 10 to about 11, or from about 10 to about 10.5, including all ranges and subranges therebetween. In one embodiment, the pH of the base composition is about 10.5.

In some embodiments, the hair color-altering base compositions according to the present disclosure are free or essentially free of cationic polymers.

Optionally, the compositions may comprise up to about 100% biodegradable, sustainable, and/or environmentally friendly raw materials, such as up to about 99%, up to about 98%, up to about 97%, up to about 96%, or up to about 95%.

Hair color-altering base compositions according to the disclosure are typically in the form of a cream, paste, or lotion, but may also be in the form of a serum, a gel, a gel cream, or the like. In some embodiments, the hair color-altering base compositions may be a rinse-off hair dye product, that can be used to lift hair color or provide desired color to the hair after being mixed with a developer composition comprising an oxidizing agent. Hair color-altering base compositions according to the disclosure are generally stable and can be stored at room temperature for at least 24 months.

Hair color-altering base compositions disclosed herein can be mixed with a developer composition (developing composition, or developer) that comprises an oxidizing agent, resulting in mixtures, i.e., hair color-altering compositions, that are suitable for applying onto the hair for altering the color of the hair, including lifting the color of hair and/or providing color to the hair, and at the same time, providing benefits such as maintaining and/or enhancing the strength of the hair, and reducing damage to hair due to chemical treatment during altering the color of the hair.

Developer Compositions

Developer compositions (also referred to as oxidizing compositions) can be mixed with hair color-altering base compositions according to the disclosure to prepare a composition for altering the color of the hair. Typically, a developer composition comprises at least one oxidizing agent and a cosmetically suitable carrier. Developer compositions that can be used to prepare a hair color-altering composition according to the disclosure are not limited, and can include, for example, any commercial developer composition as long as it includes at least one oxidizing agent.

In various embodiments, a suitable oxidizing agent may be chosen, for example, from peroxides, such as hydrogen peroxide and urea peroxide; persalts, such as persulfates, perborates, percarbonates, peroxygenated salts, etc., alkali metal bromates, alkali metal ferricyanides, alkali metal carbonates, or a mixture thereof. An oxidizing agent may also be chosen from one or more oxidation-reduction enzymes, such as laccases, peroxidases, and 2-electron oxidoreductases (such as uricase), optionally in the presence of their respective donor or cofactor.

In one embodiment, a suitable oxidizing agent may be chosen from persulfates and/or monopersulfates such as, for example, potassium persulfate, sodium persulfate, ammonium persulfate, as well as mixtures thereof. In one embodiment, the oxidizing agents in the present disclosure are chosen from hydrogen peroxide, potassium persulfate, sodium persulfate, and mixtures thereof.

In certain embodiments, hydrogen peroxide is used as an oxidizing agent. In certain situations, hydrogen peroxide may be present in an aqueous developer whose titer may range from 1 to 40 volumes, such as from 5 to 40 volumes, from 5 to 30 volumes, or from 5 to 20 volumes. In certain embodiments, the oxidizing component is a 10V, 20V, 30V, or 40V hydrogen peroxide developer composition.

The oxidizing agent may, in various embodiments, be present in the developer composition in an amount ranging from about 0.05% to about 50% by weight, such as from about 0.1% to about 30% by weight, from about 0.1% to about 20% by weight, about 1% to about 20%, about 1% to about 15%, about 1% to about 12%, about 3% to about 20%, about 3% to about 15%, about 3% to about 12%, about 5% to about 20%, about 5% to about 15%, about 5% to about 12%, about 7% to about 20%, about 7% to about 15%, about 7% to about 12%, about 9% to about 20%, about 9% to about 15%, or about 9% to about 12% by weight, based on the total weight of the developer composition.

The developer composition may contain at least one solvent, chosen from, for example water, organic solvents, or mixtures thereof. Suitable organic solvents for use in the developer composition, alone or in mixture with water, include but are not limited to ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, or mixtures thereof.

The organic solvents for use in the developer compositions can be volatile or non-volatile compounds. The organic solvent may, for example, be present in an amount ranging from about 0.5% to about 70% by weight, such as from about 2% to about 60% by weight, such as from about 5 to about 50% by weight, relative to the total weight of the developer composition.

The developer compositions are typically aqueous, but may also be in the form of a powder, gel, liquid, foam, lotion, cream, mousse, or emulsion. For instance, in certain embodiments the developer composition is aqueous and is in the form of a liquid, cream, or emulsion. In alternative embodiments, the developer composition may be anhydrous or substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers for example to bound water, such as the water of crystallization of the salts or traces of water absorbed by the raw materials used in the preparation of the compositions according to embodiments of the disclosure. When the developer composition is substantially anhydrous, the developer composition may comprise at least one solvent chosen from organic solvents described above.

The developer compositions may optionally include other components typically used in developer compositions, such as, for example, rheology-modifying agents, chelants, fatty substances, ceramides, pH adjusting agents, preservatives, fragrances, surfactants, etc.

The pH of the developer composition is typically below 7. In some embodiments, the pH of the developer composition may be below 4.

Hair Color-Altering Compositions

In non-limiting embodiments, the disclosure also provides hair color-altering compositions, which comprise components described above and at least one oxidizing agent. The hair color-altering compositions are typically prepared by mixing a hair color-altering base composition disclosed herein with a developer composition, for example at or near the time of use.

According to various embodiments, a hair color-altering base composition disclosed herein can be mixed with a developer composition in a weight ratio of hair color-altering base composition to developer that ranges from about 1:5 to about 5:1, such as from about 1:4 to about 4:1, about 1:3 to about 3:1, or about 1:2 to about 2:1, or is, for example, about 5:1, about 4:1, about 3:1, about 2:1, about 1.5:1, about 1:1, about 1:1.5, about 1:2, about 1:3, about 1:4, or about 1:5.

In various embodiments, the hair color-altering compositions according to the present disclosure may be free or essentially free of cationic polymers. In some embodiments, the compositions disclosed herein are free or essentially free of ammonia, salts thereof, and/or hydrates thereof. While in some other embodiments, the compositions disclosed herein may comprise ammonia, salts thereof, and/or hydrates thereof.

The pH of the hair color-altering composition resulting from mixing together the hair color-altering base composition and the developer composition is typically greater than 7, which can be adjusted to the desired value using acidifying/alkalizing agents that are well known in the art. In certain embodiments, the pH of the hair color-altering composition is from about 7 to about 12, such as from about 8 to about 12, from about 9 to about 12, from about 7 to about 11, from about 8 to about 11, from about 9 to about 11. In some embodiments, the hair color-altering composition has a pH ranges from about 10 to about 11.

II. Kits

The present disclosure also relates to kits comprising the base compositions and/or developer compositions described herein. The kits in various embodiments may comprise at least one container suitable for containing and/or dispensing the base compositions and/or developer compositions described herein. In some other embodiments, a kit may comprise a first container containing a hair color-altering base composition according to the disclosure, a second container comprising a developer comprising at least one oxidizing agent described above, and optionally, an additional separate container comprising a cosmetic composition, for example, a shampoo, a conditioner, a hair mask, a hair styling composition, or a hair treatment composition other than a developer or a base described above. The hair color-altering base composition and the developer composition contained in separate containers may be mixed prior to the application onto hair.

III. Methods

Compositions described herein can effectively alter the color of hair, while at the same time surprisingly provide fiber strength and/or minimize or reduce damage to the hair caused by chemical treatment. Therefore, another aspect of the disclosure relates to methods of using any of the compositions disclosed herein for altering the color of the hair, including lifting the color of hair and/or providing a desired color to the hair, while at the same time improving fiber integrity of the hair and/or minimizing or reducing damage to the hair caused by chemical treatment.

In various embodiments, the methods disclosed herein typically comprise applying to hair an effective amount of a hair color-altering composition disclosed herein. The hair color-altering composition is generally obtained at the time or near the time of use by mixing a hair color-altering base composition disclosed herein and a developer composition comprising at least one oxidizing agent. In some embodiments, the methods may further include mixing a hair color-altering base composition disclosed herein and a developer composition described herein at the time or near the time of use.

In various embodiments, before application of the compositions disclosed here, the hair may be bleached, shampooed, and/or rinsed. In some embodiments, before application of the hair color-altering composition to the hair, the hair may be first cleansed with a commercially available shampoo or be rinsed with water. The hair may be further conditioned and/or rinsed after shampooing and before application of the compositions disclosed herein. After the hair is shampooed, conditioned, and/or rinsed, the hair color-altering composition is then applied to the washed or rinsed hair when the hair is wet, damp, or moist. In some other embodiments, before applying the hair color-altering composition to the hair, the hair can optionally be moistened, damped, or wetted by water spray or using a wet towel, or by applying other treatment compositions that make the hair moist, damp, or wet. In some embodiments, after the application of the compositions disclosed to the hair, the hair may be further rinsed, shampooed, and/or conditioned one or more times.

As used herein, the term "effective amount" refers to any amount sufficient to provide a desired lifting or coloring effect. For example, in some embodiments, from about 0.1 grams to about 50 grams of a hair color-altering composition may be applied to the hair, depending on the specific product formulation, hair length, hair volume, and hair color. In some embodiments, about 0.1 grams (g) of the composition per gram of hair is applied to the hair. In some embodiments, about 0.5 grams (g) of the composition per gram of hair is applied to the hair. The composition applied to the hair may be distributed through the hair as desired, e.g. substantially evenly or uniformly massaged throughout the hair by combing through with fingers or a means such as a comb or the like.

After the hair color-altering composition is applied on to the hair, the composition may be allowed to remain on the hair for a period of time sufficient to impart the benefits provided by the composition ("leave-in period"), such as lifting effect or providing desired color or tone to the hair. For example, the hair color composition may be left on the hair for up to one hour, such as from about 1 minute to about 60 minutes, from about 1 minutes to about 45 minutes, from about 1 minute to about 30 minutes, from about 1 minute to about 20 minutes, from about 1 minute to about 15 minutes, from about 1 minute to about 10 minutes, from about 1 minute to about 5 minutes, from about 3 minutes to about 45 minutes, from about 5 minutes to about 30 minutes, or from about 10 minutes to about 20 minutes, and then rinsed off from the hair. One skilled in the art will, by considering various factors such as the starting color of the hair and the desired color to obtained, be able to determine an appropriate amount of time to leave the hair color-altering composition or mixture on the hair in order to achieve the desired alternation in hair color. If desired, the hair applied with coloring mixtures may be further shampooed and/or conditioned after the coloring mixtures are rinsed off the hair.

In some embodiments, a method disclosed herein is for permanently coloring or dyeing hair, while improving the strength and fiber integrity to the hair. In this case, a hair color-altering base composition may include one or more coloring agents such as oxidation dyes optionally combined with one or more couplers.

Having described the many embodiments of the present invention in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated. It is to be understood that all definitions herein are provided for the present disclosure only.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the compositions.

In this application, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations. Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The term "and/or" should be understood to include both the conjunctive and the disjunctive. For example, "citric acid and/or salts thereof" means "citric acid and salts thereof" as well as "citric acid or salts thereof," and expressly covers instances of either without reference to the other.

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

All ranges and amounts given herein are intended to include sub-ranges and amounts using any disclosed point as an end point, and all endpoints are intended to be included unless expressly stated otherwise. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not expressly stated, unless expressly stated otherwise. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

As used herein, if a component is described as being present "in an amount up to" a certain amount, it is intended that such component is, in fact, present in the composition, i.e. is present in an amount greater than 0%.

All amounts given herein are relative to the amount of active material, unless otherwise indicated.

All percentages, parts and ratios herein are based upon the total weight of the compositions of the present disclosure, unless otherwise indicated.

The term "altering the color" or "color-altering" as used herein refers to lifting or lightening the color of hair. It can also refer to dyeing or coloring hair or depositing color onto the hair. In certain instances, it refers to lifting or lightening the color of hair and depositing color onto the hair at the same time.

As used herein, the terms "applying a composition onto keratin fibers" and "applying a composition onto hair" and variations of these phrases are intended to mean contacting the keratin fibers including hair, with at least one of the compositions of the disclosure, in any manner. It may also mean contacting the keratin fibers in an effective amount of the composition.

As used herein, "cosmetic composition" encompasses many types of compositions for application to keratin materials such as skin or hair, for example, hair lotions, hair creams, hair gel creams, hair conditioners, hair masques (masks), etc., which can be used either as leave-on or rinse-off treatments or products.

As used herein, the term "inorganic" means a material that does not comprise carbon.

As used herein, the term "organic" means a material that is produced substantially without or essentially without the use of synthetic materials.

As used herein, the term "salts" may include salts having a counter-ion such as an alkali metal, alkaline earth metal, or ammonium counterion. This list of counterions, however, is non-limiting. Salts also include a dissociated form of a compound, e.g. in an aqueous solution.

Bonding agents should be understood to include salts of such agents, whether or not specifically stated. Thus, a "first bonding agent chosen from citric acid" should be understood to include salts of citric acid. Likewise, a "second bonding agent chosen from glycine" should be understood to include salts of glycine.

As used herein, the term "stable" refers to that the composition does not exhibit phase separation and/or crystallization for a period of time, for example, for at least 1 day (24 hours), one week, one month, one year, or two years.

As used herein, the terms "substantially free" or "essentially free" mean the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The terms "free," "substantially free," and "essentially free" as used herein may also mean that the specific material is not added to the composition but may still be present in a raw material that is included in the composition. For example, a composition according to the disclosure may not include an added wax but may include a pigment that is coated with a wax and still be considered "free," "substantially free," or "essentially free" of waxes.

As used herein, the term "surfactants," as well as any specifically identified surfactants, includes salts of the surfactants even if not explicitly stated.

As used herein, the term "synthetic" means a material that is not of natural origin. The term "natural" and "naturally-sourced" means a material of natural origin, such as derived from plants, which also cannot be subsequently chemically or physically modified. "Plant-based" means that the material came from a plant.

As used herein, the term "treat" (and its grammatical variations) refers to the application of the compositions of the present disclosure onto the surface of keratin materials, such as hair.

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

EXAMPLES

The following examples are intended to be non-limiting and explanatory in nature only. In the Examples, amounts in each composition are expressed in percentage by weight (wt %) of active materials, unless otherwise defined, relative to the total weight of the composition.

Example 1—Hair Color-Altering Base Compositions

Exemplary base compositions 1A and 1B according to the present disclosure and comparative compositions C1-C5 were prepared by mixing the components according to the formulations set forth in Table 1. The pH of each composition was adjusted to about 10.5 at the temperature of about 25° C. All compositions were in the form of a cream and were stable for at least 24 months.

TABLE 1

|  | Inventive | | Comparative | | | | |
| --- | --- | --- | --- | --- | --- | --- | --- |
|  | 1A | 1B | C1 | C2 | C3 | C4 | C5 |
| CITRIC ACID | 0.2 | 0.2 | 0.2 | 0.5 | 0.2 | 0.5 |  |
| GLYCINE | 0.5 | 0.5 | 1.0 | 0.5 |  |  |  |
| TAURINE |  | 0.5 |  |  | 0.5 | 0.5 |  |
| CETEARYL ALCOHOL | 16.3 | 16.3 | 16.3 | 16.3 | 16.3 | 16.3 | 16.3 |
| OLEYL ALCOHOL | 2.7 | 2.7 | 2.7 | 2.7 | 2.7 | 2.7 | 2.7 |
| OLEIC ACID | 2.7 | 2.7 | 2.7 | 2.7 | 2.7 | 2.7 | 2.7 |
| BUTYROSPERMUM PARKII (SHEA) BUTTER | 4 | 4 | 4 | 4 | 4 | 4 | 4 |
| CETEARYL GLUCOSIDE | 0.5 | 0.5 | 0.5 | 0.5 | 0.5 | 0.5 | 0.5 |
| ETHANOLAMINE | 5.4 | 5.4 | 5.4 | 5.7 | 5.4 | 5.7 | 5.2 |
| GLYCERIN | 5 | 5 | 5 | 5 | 5 | 5 | 5 |
| PROPANEDIOL | 5 | 5 | 5 | 5 | 5 | 5 | 5 |
| XANTHAN GUM | 0.2 | 0.2 | 0.2 | 0.2 | 0.2 | 0.2 | 0.2 |
| TETRASODIUM GLUTAMATE DIACETATE | 0.24 | 0.24 | 0.24 | 0.24 | 0.24 | 0.24 | 0.24 |
| FRAGRANCE, PRESERVATIVES, pH ADJUSTERS, VITAMIN, PIGMENTS, etc. | <2.6 | <2.6 | <2.6 | <2.6 | <2.6 | <2.6 | <2.6 |
| WATER | QS | QS | QS | QS | QS | QS | QS |

As shown in Table 1, compositions 1A and 1B both include citric acid and glycine in a weight ratio of about 1:2.5 (citric acid to glycine). Compositions C1 and C2 respectively include citric acid and glycine in a weight ratio of 1:5 or 1:1 (citric acid to glycine). Compositions C3 and C4, while including taurine, do not include glycine. Composition C5 does not include any bonding agent.

It should be noted that the above exemplary compositions are clear compositions, which can be added with one or more oxidative base dyes and/or couplers and be formulated as compositions to provide color effects to hair. As examples, compositions incorporating one or more oxidations dyes such as hydroxybenzomorpholine, 2,4-diaminophenoxyethanol HCl, toluene-2,5-diamine (and) thioglycerin, resorcinol, and/or m-aminophenol, in individual amounts ranging from about 0.003% to about 0.9% by weight, relative to the total amount of the composition, were also prepared based on the formulations of 1A and 1B.

Example 2—Developer Composition

An exemplary 10V developer composition D set forth in Table 2 was prepared. The developer had a pH at 25° C. of about 2.2 (±0.2).

TABLE 2

| | Developer Composition D |
|---|---|
| HYDROGEN PEROXIDE | 3 |
| TRIDECETH-2 CARBOXAMIDE MEA | 0.85 |
| CETEARYL ALCOHOL | 2.28 |
| CETEARETH-25 | 0.57 |
| SODIUM SALICYLATE | 0.035 |
| GLYCERIN | 0.5 |
| TETRASODIUM PYROPHOSPHATE | 0.04 |
| TETRASODIUM ETIDRONATE | 0.06 |
| WATER | QS |

Example 3—Evaluation of Fiber Integrity of Treated Hair

The fiber integrity of pre-bleached hair treated with inventive compositions 1A and 1B was evaluated in comparison with pre-bleached hair treated with compositions C1-C5 and control pre-bleached hair via break stress testing (tensile testing).

1. Preparation of Treated Hair

Caucasian hair tresses with tone level of HT 4-5 were used in the testing. Each tress had 50 individual fibers and was about 2.7 g with a length of about 8". The hair tresses were bleached once with a standard bleaching composition for about 50 minutes at 33° C. After bleaching, the hair tresses were rinsed and washed with a standard shampoo once, and were blow-dried using a hair dryer for 2 minutes. Near or at the time of use, compositions 1A, 1B, and C1-C5 were respectively mixed with 10V developer D of Example 2 in a mix ratio of 1:1 to prepare hair color-altering compositions 1A+D, 1B+D, C1+D, C2+D, C3+D, C4+D, and C5+D. Each obtained mixture was respectively applied to a separate pre-bleached hair tress in a bath ratio of 10:1 UA, allowed to stay on the hair to process for about 20 minutes, and then rinsed off the hair. The application process was repeated up to seven times. Each tress was shampooed and blow dried for about 2 minutes, or until fully dry, between applications and after the final application. The whole process was performed at a temperature of about 27° C. on a plate in open air condition (without the use of foils). Each mixture was tested in duplicate on separate bleached hair tresses. As baseline control, two separate bleached tresses were shampooed seven times and blow dried for about 2 minutes between shampoos and after the final shampoo, without application of any hair color-altering compositions.

After the first application, the fourth application, and/or the seventh application of the mixtures, the hair tresses were subjected to break stress testing to evaluate the integrity of the hair. If statistical differences were seen after the first or the fourth application, additional applications may not be needed.

2. Break Stress Testing

The break stress of the treated hair tresses was measured using a Miniature Tensile Tester (MTT-US1.3) at a traction speed of about 10 mm/min when the hair tresses were in the wet state after equilibration at room temperature and 80% relative humidity. The measured results of the hair break stress after the fourth application were statistically analyzed using R software version 3.0.2, where the statistical significance level was set at $p<0.05$. The statistical results are summarized in Table 3 and illustrated in FIG. 1. Break stress represents the force/area needed to break the hair fiber. A higher break stress represents a stronger and stiffer hair fiber.

TABLE 3

| Testing Cell | Mixture (Base Composition + Developer D) (1:1) | Break Stress (MPa) | | | | |
|---|---|---|---|---|---|---|
| | | Mean | Standard Deviation | CI* (95%) | CV** (%) | Count |
| A | C5 + D | 99.9 | 26.1 | [92; 107.8] | 26.1 | 42 |
| B | C3 + D | 107 | 22.1 | [100.74; 113.26] | 20.8 | 48 |
| C | C4 + D | 103 | 23.3 | [96.41; 109.59] | 22.7 | 48 |
| D | 1A + D | 114 | 20.8 | [107.77; 120.23] | 18.3 | 43 |
| E | C1 + D | 105 | 23.1 | [97.74; 112.26] | 22.1 | 39 |
| F | C2 + D | 108 | 21 | [102.07; 113.93] | 19.4 | 48 |
| G | 1B + D | 114 | 15.9 | [109.3; 118.7] | 13.9 | 44 |
| H | Baseline Control | 120 | 20.5 | [113.79; 126.21] | 17.1 | 42 |

*CI: confidence interval estimate
**CV: coefficient of variation

As shown in Table 3 and FIG. 1, the process of altering the color of the pre-bleached hair using compositions with no bonding agents (C5+D) resulted in hair that had a significantly decreased break stress value, indicating that the hair was less strong and more damaged compared to the hair not being treated with a color-altering composition (baseline control). In contrast, as shown in FIG. 1 and Table 3, the hair treated with the mixtures of 1A+D or 1B+D, which include a bonding system according to the disclosure, surprisingly demonstrated statistically significant improvement in break stress value compared to the hair treated with the mixture of C5+D ($p<0.05$). This result demonstrates that hair treated with compositions according to the disclosure had greater fiber integrity and strength, and less damage, even after being subjected to a chemical hair color altering process, compared to hair subjected to the same process but without the beneficial bonding agents according to the disclosure.

The results also show that the break stress values of the hair treated with the mixture of C1+D, C2+D, C3+D, or C4+D, which included bonding agents but not according to the disclosure, was not statistically improved, compared to the break stress of the hair treated with the mixture of C5+D ($p>0.05$). This result demonstrates that hair treated with compositions according to the disclosure had greater fiber integrity and strength, and less damage, even after being subjected to a chemical hair color altering process, compared to hair subjected to the same process but without the synergistic combination of bonding agents according to the disclosure.

The above data demonstrated that the synergistic combination included in the claimed bonding system, along with other components in an oxidative system disclosed herein, when applied to hair in the presence of an oxidizing agent, unexpectedly provides statistical improvement on hair fiber integrity and minimized further damage to the hair due to the process of altering the color of the hair.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

The invention claimed is:

1. A composition for altering the color of keratin fibers comprising:
   (a) a bonding system comprising:
      (i) at least one first bonding agent chosen from alpha-hydroxy acids comprising at least three hydrogen donor carboxyl groups and/or salts thereof;
      (ii) at least one second bonding agent chosen from glycine and/or salts thereof; and
      (iii) optionally, at least one third bonding agent chosen from amino sulfonic acids and/or salts thereof;
         wherein the weight ratio of the total amount of first bonding agent(s) to second bonding agent(s) ranges from about 1:5 to about 1:1;
   (b) at least one fatty alcohol;
   (c) at least one fatty acid;
   (d) at least one alkyl polyglucoside;
   (e) at least one alkalizing agent; and
   (f) at least one solvent comprising water;
   wherein the pH of the composition is greater than 7, and wherein the composition is essentially free of cationic polymers.

2. The composition of claim 1, wherein the composition further comprises from about 0.0001% to about 10% by weight, relative to the total weight of the composition, of at least one hair color-altering agent chosen from oxidation dyes, couplers, or combinations thereof.

3. The composition of claim 1, comprising at least one first bonding agent chosen from citric acid, salts thereof, or mixtures thereof.

4. The composition of claim 1, wherein the weight ratio of the first bonding agent(s) to the second bonding agent(s) ranges from about 1:45 to about 1:15.

5. The composition of claim 1, wherein the weight ratio of the first bonding agent(s) to the second bonding agent(s) is about 1:2.5.

6. The composition of claim 1, wherein the total amount of the first bonding agent(s) ranges from about 0.1% to about 0.4% by weight, relative to the total weight of the composition.

7. The composition of claim 1, wherein the total amount of the second bonding agent(s) is greater than 0.1% and less than 2% by weight, relative to the total weight of the composition.

8. The composition of claim 1 comprising at least one third bonding agent, wherein the total amount of the third bonding agent(s) is greater than 0.1% and less than 2% by weight, relative to the total weight of the composition.

9. The composition of claim 1, wherein:
   the at least one fatty alcohol is chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, isotridecyl alcohol, cis-4-t-butylcyclohexanol, myricyl alcohol, or mixtures thereof; and
   the total amount of fatty alcohol(s) ranges from about 0.5% to about 25% by weight, relative to the total weight of the composition.

10. The composition of claim 1, wherein:
    the at least one fatty acid is chosen from myristic acid, lauric acid, palmitic acid, stearic acid, behenic acid, arichidonic acid, oleic acid, isostearic acid, sebacic acid, or mixtures thereof; and
    the total amount of fatty acid(s) ranges from about 0.5% to about 15% by weight, relative to the total weight of the composition.

11. The composition of claim 1, further comprising at least one vegetable oil, wherein the total amount of vegetable oil(s) ranges from about 0.5% to about 15% by weight, relative to the total weight of the composition.

12. The composition of claim 1, wherein the total amount of alkyl polyglucoside(s) ranges from about 0.05% to about 5% by weight, relative to the total weight of the composition.

13. The composition of claim 1, wherein the at least one alkalizing agent is chosen from organic alkalizing agents, mineral alkalizing agents, or combination thereof.

14. The composition of claim 13, wherein:
    the total amount of organic alkalizing agents, when present, ranges from about 0.1% to about 10% by weight, relative to the total weight of the composition; and
    the total amount of mineral alkalizing agents, when present, ranges from about 0.1% to about 15% by weight, relative to the total weight of the composition.

15. The composition of claim 1, further comprising at least one thickening agent, wherein the total amount of thickening agent(s) ranges from about 0.05% to about 5% by weight, relative to the total weigh of the composition.

16. The composition of claim 1, further comprising at least one polyol, wherein the total amount of polyol(s) is at least 0.5% by weight, relative to the total weight of the composition.

17. A composition for altering the color of keratin fibers comprising:
    (a) a bonding system comprising:
       (i) at least one first bonding agent chosen from citric acid and/or salts thereof, wherein the total amount of citric acid and salts thereof ranges from about 0.1% to about 0.4%;
       (ii) at least one second bonding agent chosen from glycine and/or salts thereof, wherein the total amount of glycine and salts thereof is greater than 0.1% and less than 2%; and
       (iii) optionally, at least one third bonding agent chosen from taurine and/or salts thereof, wherein the total amount of taurine and salts thereof is greater than 0.1% and less than 2%;
          wherein the weight ratio of the total amount of first bonding agent(s) to second bonding agent(s) ranges from about 1:5 to about 1:1;
    (b) at least one fatty alcohol;
    (c) at least one fatty acid;
    (d) at least one alkyl polyglucoside;
    (e) at least one alkalizing agent;

(f) at least one hair color-altering agent chosen from oxidation dyes, couplers, or combinations thereof;
(g) at least one solvent comprising water;
(h) optionally, at least one vegetable oil;
(i) optionally, at least one thickening agent; and
(j) optionally, at least one polyol;
wherein all amounts are by weight, based on the total weight of the composition;
wherein the pH of the composition is greater than 7; and
wherein the composition is essentially free of cationic polymers.

18. A method for altering the color of hair comprising:
applying to the hair a hair color-altering composition; and
rinsing the hair color-altering composition from the hair after a leave-in period;
wherein the hair color-altering composition comprises:
(a) a bonding system comprising:
  (i) at least one first bonding agent chosen from alpha-hydroxy acids comprising at least three hydrogen donor carboxyl groups and/or salts thereof;
  (ii) at least one second bonding agent chosen from glycine and/or salts thereof; and
  (iii) optionally, at least one third bonding agent chosen from amino sulfonic acids and/or salts thereof;
    wherein the weight ratio of the total amount of first bonding agent(s) to second bonding agent(s) ranges from about 1:5 to about 1:1;
(b) at least one fatty alcohol;
(c) at least one fatty acid;
(d) at least one alkyl polyglucoside;
(e) at least one alkalizing agent;
(f) at least one hair color-altering agent chosen from oxidation dyes, couplers, or combinations thereof;
(g) at least one oxidizing agent;
(h) at least one solvent comprising water;
(h) optionally, at least one vegetable oil;
(i) optionally, at least one thickening agent; and
(j) optionally, at least one polyol;
  wherein the pH of the hair color-altering composition is greater than 7, and
  wherein the composition is essentially free of cationic polymers.

* * * * *

UNITED STATES PATENT AND TRADEMARK OFFICE
CERTIFICATE OF CORRECTION

PATENT NO. : 12,144,879 B2
APPLICATION NO. : 17/877999
DATED : November 19, 2024
INVENTOR(S) : Jennifer Elie et al.

Page 1 of 1

It is certified that error appears in the above-identified patent and that said Letters Patent is hereby corrected as shown below:

In the Claims

Claim 15, Column 42, Line 41, change "weigh" to -- weight --.

Signed and Sealed this
Twenty-fifth Day of March, 2025

Coke Morgan Stewart
*Acting Director of the United States Patent and Trademark Office*